US010301597B2

(12) United States Patent
Lipke et al.

(10) Patent No.: US 10,301,597 B2
(45) Date of Patent: *May 28, 2019

(54) ENCAPSULATION AND CARDIAC DIFFERENTIATION OF HIPSCS IN 3D PEG-FIBRINOGEN HYDROGELS

(71) Applicant: Auburn University, Auburn, AL (US)

(72) Inventors: Elizabeth A. Lipke, Auburn, AL (US); Petra Kerscher, Auburn, AL (US); Alexander J. Hodge, Auburn, AL (US)

(73) Assignee: Auburn University, Auburn, AL (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/411,807

(22) Filed: Jan. 20, 2017

(65) Prior Publication Data
US 2017/0198256 A1 Jul. 13, 2017

Related U.S. Application Data

(63) Continuation of application No. 14/538,435, filed on Nov. 11, 2014, now Pat. No. 9,587,221.

(60) Provisional application No. 61/902,453, filed on Nov. 11, 2013.

(51) Int. Cl.
C12N 5/077 (2010.01)
C12N 5/074 (2010.01)

(52) U.S. Cl.
CPC ......... *C12N 5/0657* (2013.01); *C12N 5/0696* (2013.01); *C12N 2500/46* (2013.01); *C12N 2500/50* (2013.01); *C12N 2501/999* (2013.01); *C12N 2506/45* (2013.01); *C12N 2513/00* (2013.01); *C12N 2533/52* (2013.01); *C12N 2533/54* (2013.01); *C12N 2537/10* (2013.01)

(58) Field of Classification Search
None
See application file for complete search history.

(56) References Cited

U.S. PATENT DOCUMENTS 7,842,667 B2 11/2010 Seliktar et al.

FOREIGN PATENT DOCUMENTS

| WO | 2005061018 | 7/2005 |
| WO | 2011073991 | 6/2011 |
| WO | 2013056072 | 4/2013 |

OTHER PUBLICATIONS

Amit et al., "Dynamic suspension culture for scalable expansion of undifferentiated human pluripotent stem cells", Nature Protocols, vol. 6, No. 5, pp. 572-579. Apr. 7, 2011.

Baharvand et al., "The effect of extracellular matrix on embryonic stem cell-derived cardiomyocytes", Journal of Molecular and Cellular Cardiology, 38, pp. 495-503. Dec. 31, 2005.

Beers et al., "Passaging and colony expansion of human pluripotent stem cells by enzyme-free dissociation in chemically defined culture conditions", Nat Protoc, 7(11), pp. 2029-2040. Dec. 31, 2012.

Bird et al., "The human adult cardiomyocyte phenotype", Cardiovascular Research 58, pp. 423-434. Dec. 31, 2003.

Burridge et al., "Chemically defined generation of human cardiomyocytes", Nature Methods, vol. 11, No. 8, pp. 855-864. Jun. 15, 2014.

Burridge et al., "A Universal System for Highly Efficient Cardiac Differentiation of Human Induced Pluripotent Stem Cells That Eliminates Interline Variability", PLoS ONE, vol. 6, Issue 4, pp. 1-17. Apr. 30, 2011.

Dikovsky et al., "The effect of structural alterations of PEG-fibrinogen hydrogel scaffolds on 3-D cellular morphology and cellular migration", Biomaterials 27, pp. 1496-1506. Oct. 21, 2005.

Dunn et al., "Biomimetic materials design for cardiac tissue regeneration", WIREs Nanomed Nanobiotechnol, vol. 6, pp. 15-39. Jan. 31, 2014.

Fink et al., "Chronic stretch of engineered heart tissue induces hypertrophy and functional improvement", The FASEB Journal, vol. 14, pp. 669-679. Apr. 30, 2000.

Franco et al., "Development and optimization of a dual-photoinitiator, emulsion-based technique for rapid generation of cell-laden hydrogel microspheres", Acta Biomaterialia 7, pp. 3267-3276. Jun. 13, 2011.

Frank et al., "Era of Faster FDA Drug Approval Has Also Seen Increased Black-Box Warnings and Market Withdrawals", Health Affairs 33, No. 8, pp. 1453-1459. Aug. 31, 2014.

Hirt et al., "Functional improvement and maturation of rat and human engineered heart tissue by chronic electrical stimulation", Journal of Molecular and Cellular Cardiology, pp. 1-10. Dec. 31, 2014.

Hodge et al., "Chapter 38—Biomimetic Materials for Cardiac Regeneration", Handbook of Biomimetics and Bioinspiration, pp. 1057-1088. Nov. 23, 2013.

Itzhaki et al., "Calcium Handling in Human Induced Pluripotent Stem Cell Derived Cardiomyocytes", PLoS ONE, vol. 6, issue 4, pp. 1-13. Apr. 30, 2011.

Kattman et al., "Stage-Specific Optimization of Activin/Nodal and BMP Signaling Promotes Cardiac Differentiation of Mouse and Human Pluripotent Stem Cell Lines", Cell Stem Cell 8, pp. 228-240. Feb. 4, 2011.

(Continued)

*Primary Examiner* — Robert M Kelly
(74) *Attorney, Agent, or Firm* — Meunier Carlin & Curfman LLC

(57) ABSTRACT

The present invention relates to the production of cell cultures and tissues from undifferentiated pluripotent stem cells using three-dimensional biomimetic materials. The resultant cell cultures or tissues can be used in any of a number of protocols including testing chemicals, compounds, and drugs. Further, the methods and compositions of the present invention further provide viable cell sources and novel cell delivery platforms that allow for replacement of diseased tissue and engraftment of new cardiomyocytes from a readily available in vitro source. The present invention includes novel methods required for the successful production of cell cultures and tissues, systems and components used for the same, and methods of using the resultant cell and tissue compositions.

15 Claims, 20 Drawing Sheets

(56) References Cited

OTHER PUBLICATIONS

Knollmann, Bjorn, "Induced Pluripotent Stem Cell-Derived Cardiomyocytes Boutique Science or Valuable Arrhythmia Model?" Circulation Research, pp. 969-977. Mar. 15, 2013.
Laflamme et al., "Heart regeneration", Nature, vol. 473, pp. 326-336. May 19, 2011.
Lasser et al., "Timing of New Black Box Warnings and Withdrawals for Prescription Medications", JAMA, vol. 287, No. 17, pp. 2215-2220. May 1, 2002.
Lei et al., "A fully defined and scalable 3D culture system for human pluripotent stem cell expansion and differentiation", PNAS, pp. E5039-E5048. Nov. 18, 2013.
Lev et al., "Differentiation Pathways in Human Embryonic Stem Cell-Derived Cardiomyocytes", Ann. N.Y. Acad. Sci. 1047, pp. 50-65. Dec. 31, 2005.
Li et al., "Rapid Transition of Cardiac Myocytes from Hyperplasia to Hypertrophy During Postnatal Development", J Mol Cell Cardiol 28, pp. 1737-1746. Dec. 31, 1996.
Lian et al., "Robust cardiomyocyte differentiation from human pluripotent stem cells via temporal modulation of canonical Wnt signaling", PNAS, pp. E1848-E1857. May 29, 2012.
Lian et al., "Directed cardiomyocyte differentiation from human pluripotent stem cells by modulating Wnt/B-catenin signaling under fully defined conditions", Nature Protocols, vol. 8, No. 1, pp. 162-175. Dec. 31, 2013.
Lieu et al., "Absence of Transverse Tubules Contributes to Non-Uniform Ca2+ Wavefronts in Mouse and Human Embryonic Stem Cell—Derived Cardiomyocytes", Stem Cells and Development, vol. 18, No. 10, pp. 1493-1500. Dec. 31, 2009.
Lou et al., "Transmural Heterogeneity and Remodeling of Ventricular Excitation-Contraction Coupling in Human Heart Failure", Circulation, pp. 1881-1897. May 3, 2011.
Lundy et al., "Structural and Functional Maturation of Cardiomyocytes Derived From Human Pluripotent Stem Cells", pp. 1-47. Dec. 31, 1991.
Mihic et al., "The effect of cyclic stretch on maturation and 3D tissue formation of human embryonic stem cell-derived cardiomyocytes", Biomaterials 35, pp. 2798-2808. Jan. 11, 2014.
Mironi-Harpaz et al., "Photopolymerization of cell-encapsulating hydrogels: Crosslinking efficiency versus cytotoxicity", Acta Biomaterialia 8, pp. 1838-1848. Jan. 13, 2012.
Mollova et al., "Cardiomyocyte proliferation contributes to heart growth in young humans", PNAS, vol. 110, No. 4, pp. 1446-1451. Jan. 22, 2013.
Wang et al., "Alginate encapsulation technology supports embryonic stem cells differentiation into insulin-producing cells", J. Biotechnol. 144(4), 2 pages. Aug. 15, 2009.
Nie et al., "Scalable Passaging of Adherent Human Pluripotent Stem Cells", PLOS ONE, vol. 9, Issue 1, pp. 1-9. Jan. 31, 2014.
Nunes et al., "Biowire: a platform for maturation of human pluripotent stem cell-derived cardiomyocytes", Nature Methods, vol. 10, No. 8, pp. 781-791. Aug. 31, 2013.
Priori et al., "Induced pluripotent stem cell-derived cardiomyocytes in studies of inherited arrhythmias", The Journal of Clinical Investigation, vol. 123, No. 1, pp. 84-91. Jan. 31, 2013.
Radisic et al., "Functional assembly of engineered myocardium by electrical stimulation of cardiac myocytes cultured on scaffolds", PNAS, vol. 101, No. 52, pp. 18129-18134. Dec. 28, 2004.
Reiser et al., "Human cardiac myosin heavy chain isoforms in fetal and failing adult atria and ventricles", Am. J. Physiol Heart Circ Physiol, 280, pp. H1814-H1820. Dec. 31, 2001.
Robertson et al., "Concise Review: Maturation Phases of Human Pluripotent Stem Cell-Derived Cardiomyocytes", Stem Cells Express, 31, pp. 829-837. Jan. 25, 2013.
Schaaf et al., "Human Engineered Heart Tissue as a Versatile Tool in Basic Research and Preclinical Toxicology", PLOS ONE, vol. 6, Issue 10, pp. 1-12. Oct. 20, 2011.
Shapira-Schweitzer et al., "Matrix stiffness affects spontaneous contraction of cardiomyocytes cultured within a PEGylated fibrinogen biomaterial", Ada Biomaterialia 3, pp. 33-41. Dec. 31, 2007.
Shiba et al., "Human ES-cell-derived cardiomyocytes electrically couple and suppress arrhythmias in injured hearts", Nature, vol. 489, pp. 322-328. Sep. 13, 2012.
Stevens et al., "Scaffold-Free Human Cardiac Tissue Patch Created from Embryonic Stem Cells", Tissue Engineering: Part A, vol. 15, No. 6, pp. 1211-1222. Dec. 31, 2009.
Thomson et al., "Embryonic Stem Cell Lines Derived from Human Blastocysts", Science, vol. 282, pp. 1145-1148. Nov. 6, 1998.
Tiburcy et al., "Terminal Differentiation, Advanced Organotypic Maturation, and Modeling of Hypertrophic Growth in Engineered Heart Tissue", Circulation Research, pp. 1105-1114. Oct. 28, 2011.
Tulloch et al., "Growth of Engineered Human Myocardium With Mechanical Loading and Vascular Coculture", Circulation Research, 30 pages. Jun. 24, 2011.
Turnbull et al., "Advancing functional engineered cardiac tissues toward a preclinical model of human myocardium", The FASEB Journal article, vol. 28, pp. 1-11. Oct. 30, 2013.
Wei et al., "T-Tubule Remodeling During Transition From Hypertrophy to Heart Failure", Circulation Research, pp. 520-531. Aug. 20, 2010.
Yang et al., "Maturation of Human Pluripotent Stem Cell-Derived Cardiomyocytes", Circulation Research, pp. 511-524. Jan. 31, 2014.
Zhang et al., "Tissue-engineered cardiac patch for advanced functional maturation of human ESC-derived cardiomyocytes", Biomaterials 34, pp. 5813-5820. May 2, 2013.
Ziman et al., "Quantitative Measurement of Ca2+ in the Sarcoplasmic Reticulum Lumen of Mammalian Skeletal Muscle", Biophysical Journal, vol. 99, pp. 2705-2714. Oct. 31, 2010.
Zimmermann et al., "Tissue Engineering of a Differentiated Cardiac Muscle Construct", Circulation Research, 22 pages. Feb. 8, 2002.
Zweigerdt et al., "Scalable expansion of human pluripotent stem cells in suspension culture", Nature protocols, vol. 6, issue 5, pp. 689-700. Dec. 31, 2011.
Kerscher, et al. (2016) "Direct hydrogel encapsulation of pluripotent stem cells enables ontomimetic differentiation and growth of engineered human heart tissues", Biomaterials, 83: 383-95.
Zhong, et al. (2014) "Generation of three dimensional retinal tissue with functional photoreceptors from human PSCs", Nature Communications, 5: 4047, provided from HHS Public Access, Author manuscript, Mar. 23, 2015, 31 pages long.
Lu, et al. (2011) "Uses of cardiomyocytes generated from induced pluripotent stem cells", Stem Cell Research & Therapy, 2(44) : 1-10.
Bratt-Leal, et al. (2009) "Engineering the Embryoid Body Microenvironment to Direct Embryonic Stem Cell Differentiation", Biotechnology Progress, 25(1 ): 43-51.
Zwi et al., "Cardiomyocyte Differentiation of Human Induced Pluripotent Stem Cells", Circulation, 13 pages. Sep. 28, 2009.
Zwi-Dantsis et al., "Derivation and cardiomyocyte differentiation of induced pluripotent stem cells from heart failure patients", European Heart Journal Advance Access, pp. 1-12. May 22, 2012.

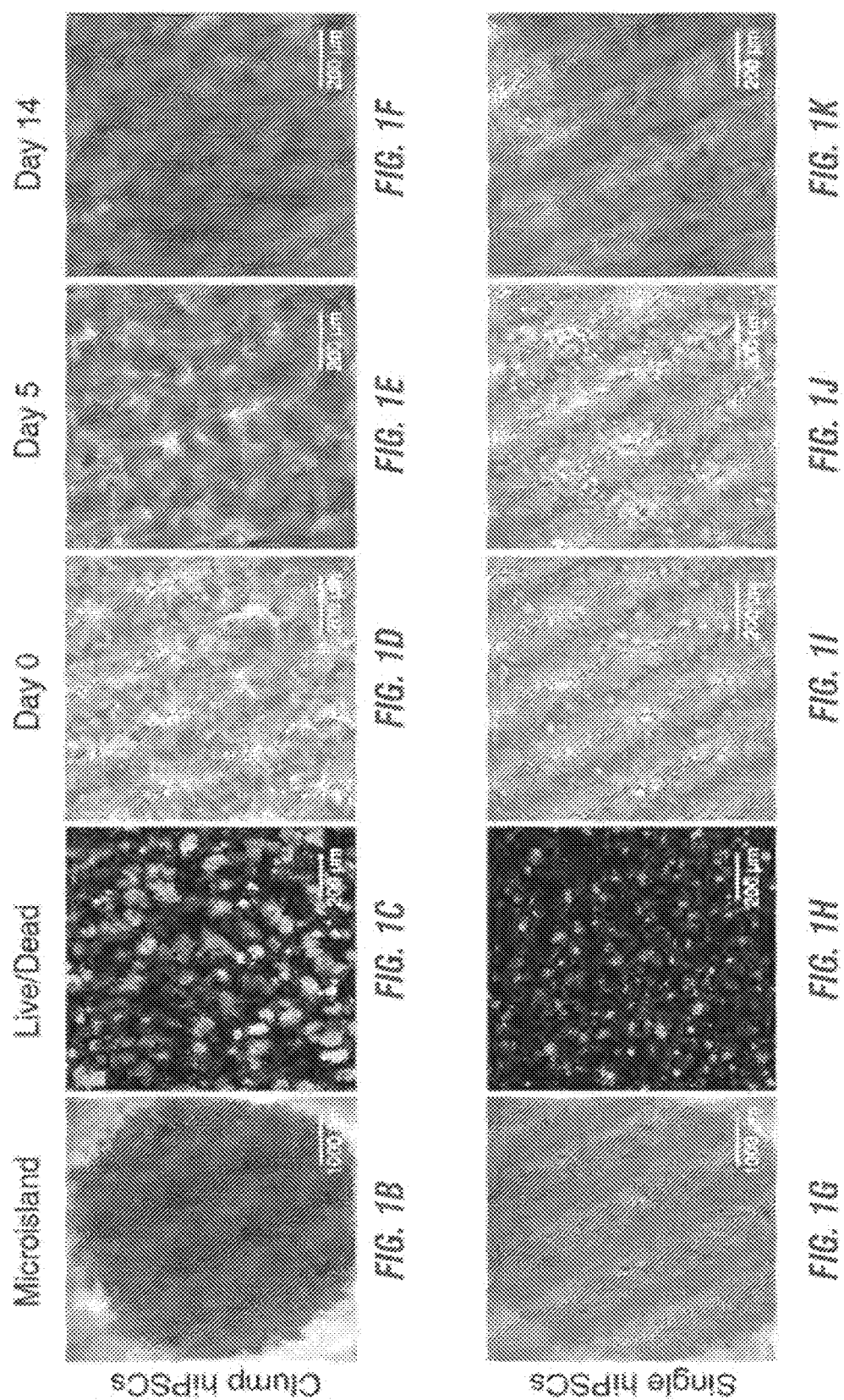

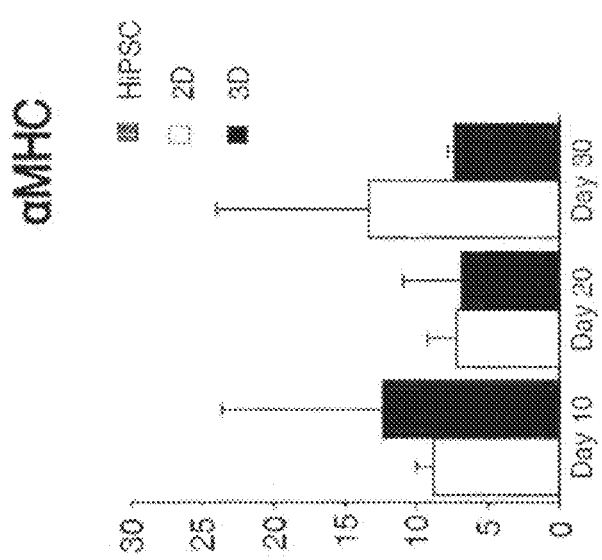
FIG. 3C
FIG. 3B
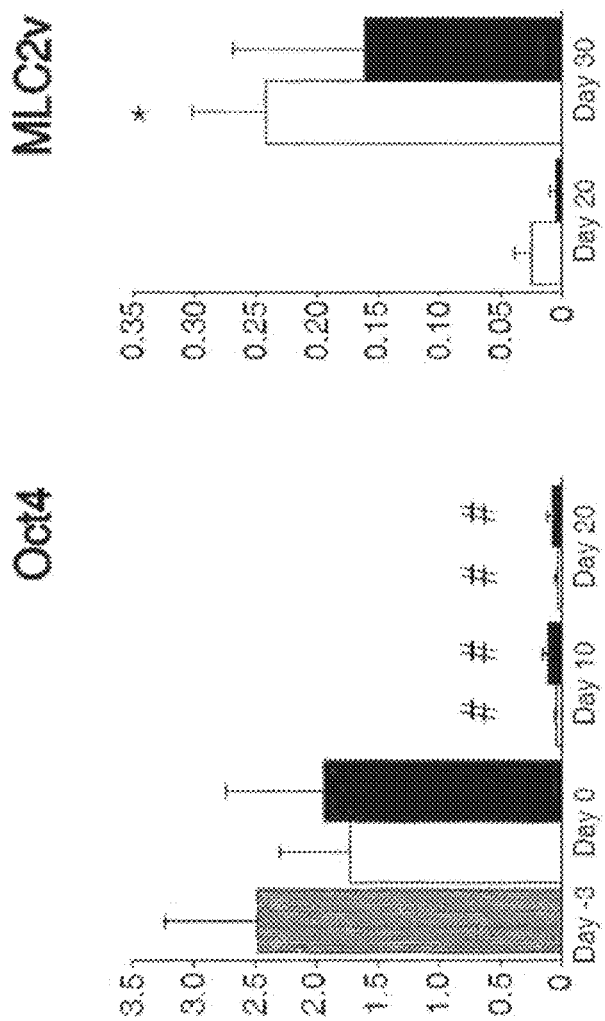
FIG. 3A

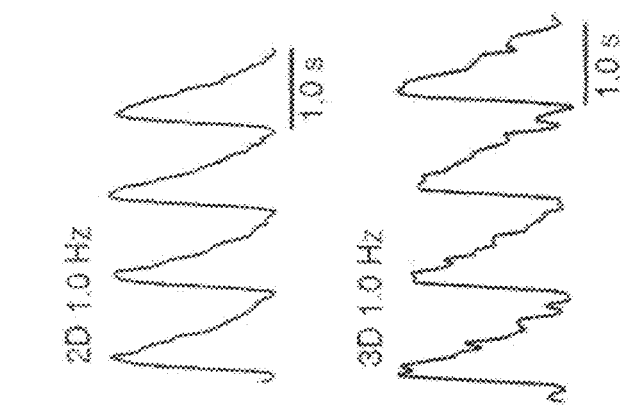
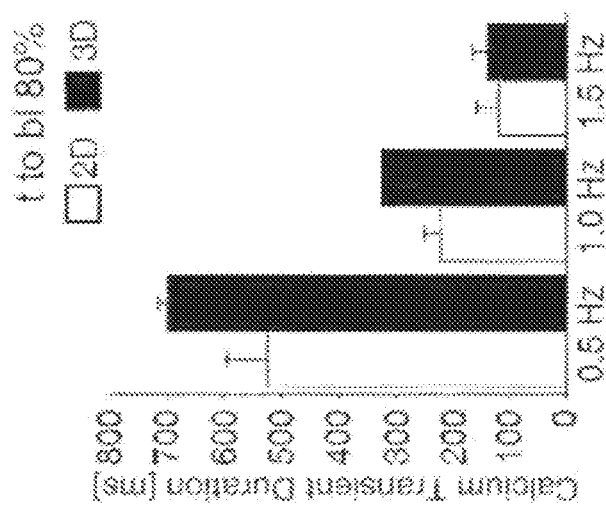
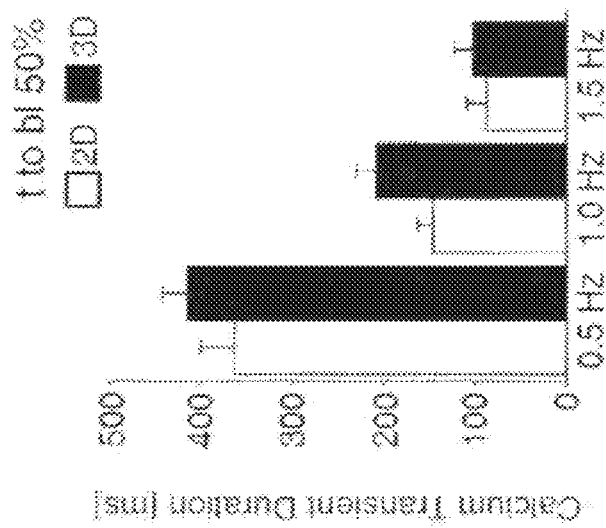
FIG. 4A
FIG. 4B
FIG. 4C

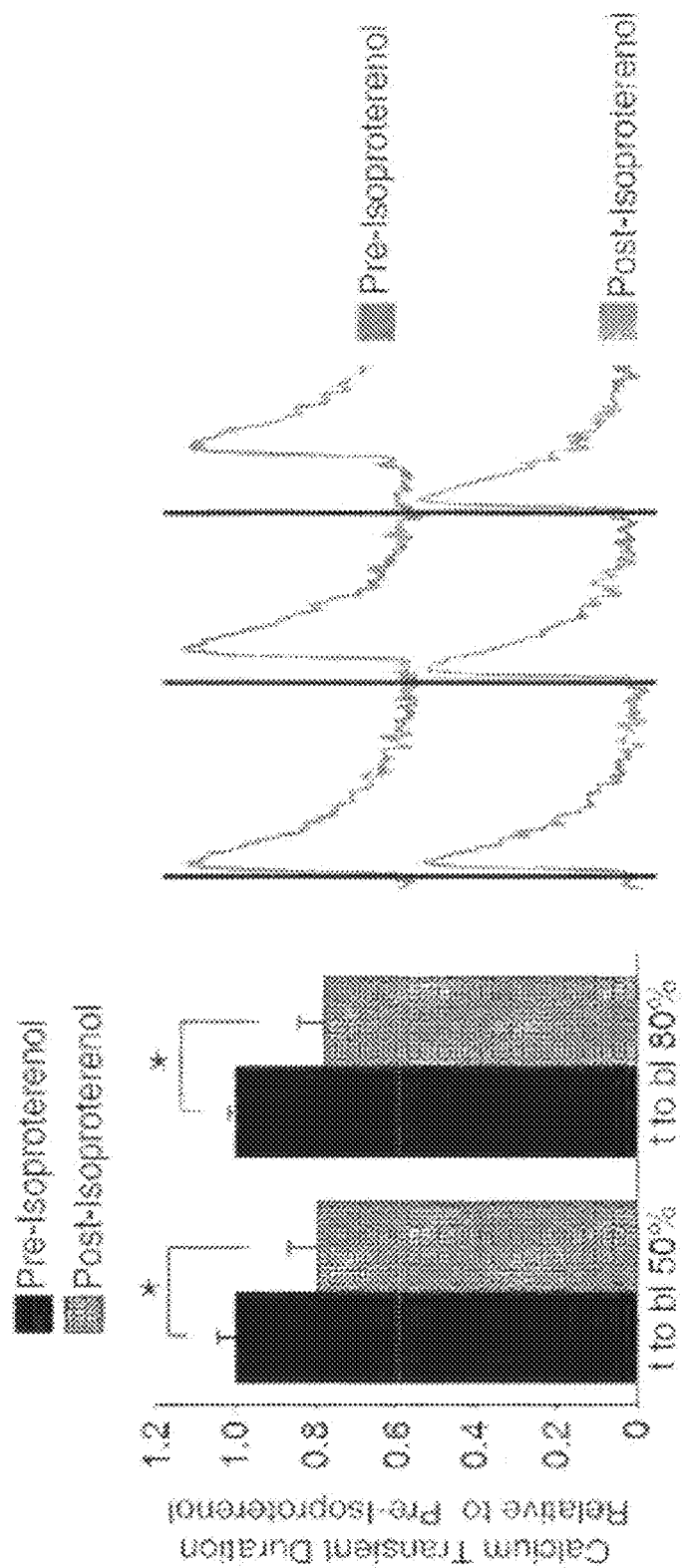

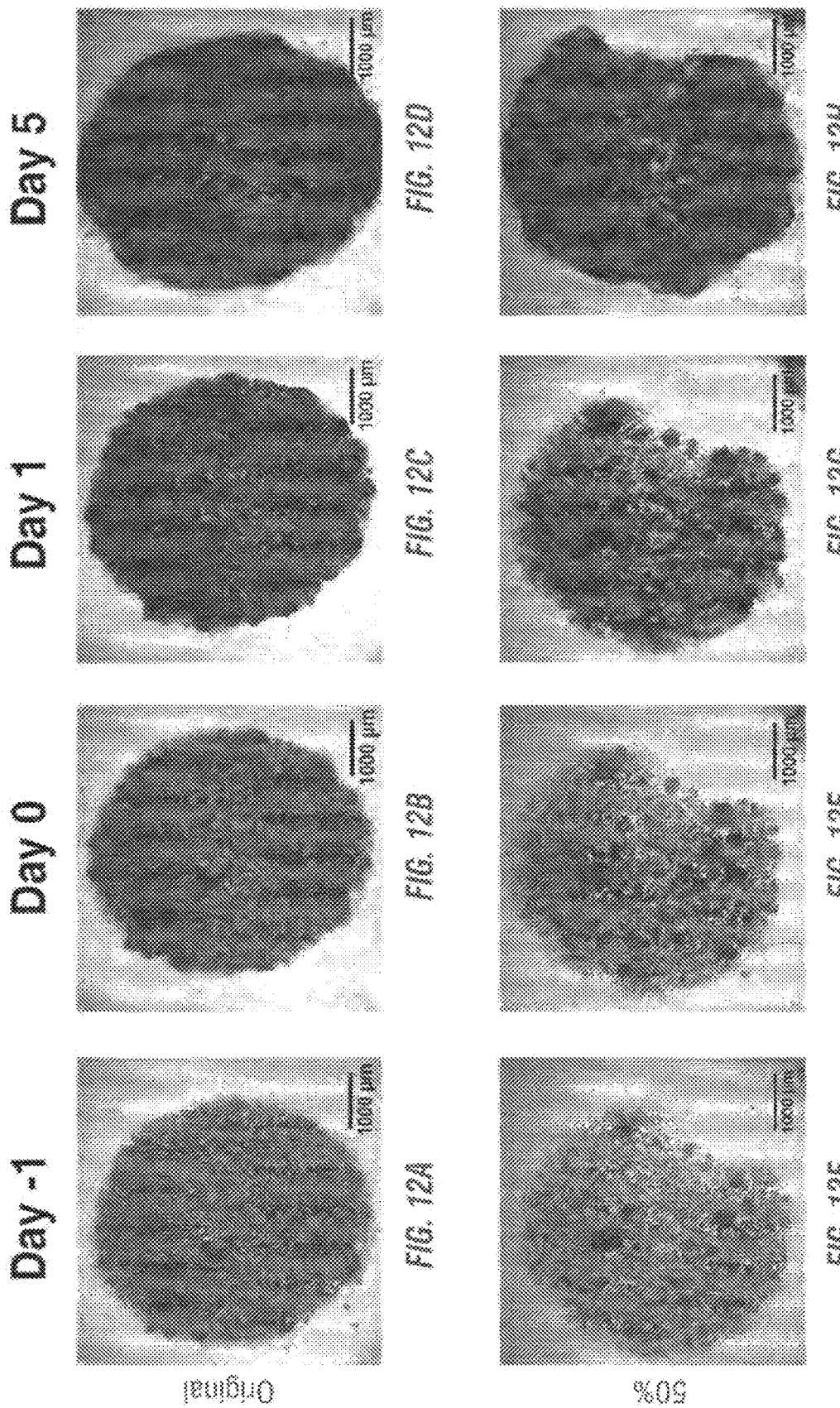

ENCAPSULATION AND CARDIAC DIFFERENTIATION OF HIPSCS IN 3D PEG-FIBRINOGEN HYDROGELS

CROSS REFERENCE TO RELATED APPLICATION

This application is a continuation of U.S. Pat. No. 9,587,221, filed Nov. 11, 2014, which claims priority under 35 U.S.C. § 119 to provisional application Ser. No. 61/902,453 filed Nov. 11, 2013, each of which is herein incorporated by reference in its entirety.

GRANT REFERENCE

This invention was made with government support under Contract No. CBET-1150854, awarded by the National Science Foundation. The government has certain rights in the invention.

BACKGROUND OF THE INVENTION

Stem cells are undifferentiated cells that possess two hallmark properties; self-renewal and the ability to differentiate into one or more different cell lineages. The process of self-renewal involves the self-replication of a stem cell to allow for propagation and expansion, wherein the stem cell remains in an undifferentiated state. Progenitor cells are also undifferentiated cells that have the ability to differentiate into one or more cell lineages, but have limited or no ability to self-renew. When maintained in culture, undifferentiated cells, such as stem or progenitor cells, can undergo spontaneous differentiation, thereby losing the desired, undifferentiated cell phenotype. Thus, culture methods that minimize spontaneous differentiation in order to maintain the undifferentiated stem or progenitor cell state are needed.

Pluripotent stem cells (PSCs) provide the potential to produce large quantities of physiologically relevant cells and tissues in vitro, including for example cardiac cells, through directed differentiation. Cells and tissues derived from PSCs have the ability to revolutionize high-throughput drug screening, modeling of human disease, such as cardiac diseases, and eventually the field of regenerative medicine. For example, predicting cardiac toxicity and the triggering of cardiac arrhythmias represents a major hurdle for pharmaceutical compound development, resulting in about 20-30% drug withdrawal from the market.

Tissue regeneration is especially critical for tissues that are unable to be repaired by the body or current medical technologies. PSC-derived tissues are of particular interest for diseases afflicting the cardiac and neural systems, as well as for production of insulin-producing cells and hematopoietic stem cells. In addition, human induced PSCs (hiPSCs) offer the potential for autologous tissue regeneration of organs and cells. Further, for treatment of genetic diseases, for example, genetic defects could be repaired prior to differentiation of hiPSCs. Examples of cardiac disease that could be treated using such an approach include tissue or cell production for patients with Timothy-syndrome, muscular dystrophy, etc. Examples of particular cardiac regeneration applications include, but are not be limited to, repair of damage to the myocardium post-myocardial infarct, treatment of cardiomyopathy/heart failure (brought about by a range of causes), repair conducting cardiac tissues (to replace current pacemaker devices)/treatment of arrhythmias, augmentation of myocardial wall stiffness to improve valve function/slow heart disease progression/prevent heart failure, and repair of congenital heart defects.

Heart disease ranks as the highest cause of mortality in the United States, affecting over 27 million Americans and responsible for over 616,000 deaths in 2006. In 2008, ischemic heart disease was the world's leading cause of death killing an estimated 7.3 million people, representing 12.8% of the world's total mortality. While heart disease comes in many different forms, five categories account for the majority of cardiac-related mortality: ischemic heart disease (myocardial infarction, or MI), hypertension, valvular degeneration, nonischemic (primary) myocardial pathologies, and congenital heart defects. Aspects of several of these categories play a role in the pathogenesis of other categories, making clear boundaries between them difficult to define. The yearly cost for treatment of all forms of heart disease is estimated to exceed $560 billion by the year 2015.

Cardiac regeneration strategies have the potential to benefit people suffering from several categories of heart disease, including ischemic heart disease, cardiomyopathies, valvular heart disease, and congenital heart defects. The use of biomimetic materials to regenerate the heart is dictated largely by the anatomy and physiology of the healthy heart and the diseases of the heart that can lead to the need for regeneration. It is also important to appreciate the capabilities and limitations of current clinical treatments. Myocardial tissue is composed of cardiac muscle, which generates the force responsible for blood pumping. Regeneration of myocardial tissue is one of the primary goals of cardiac regeneration. Appropriate mechanical and electrical function is critical for successful heart regeneration. Contraction of cardiac muscle is driven by electrical action potentials that are initiated by cardiomyocytes in the sinoatrial node. Although patients with heart disease often experience improvement in quality of life following clinical treatment, these therapies do not directly repair damaged myocardium. Furthermore, because the tissue is never directly restored to its prior health, individuals may never regain their original cardiovascular function and may experience other debilitating cardiac conditions as time progresses. In order to alleviate the long-term consequences of cardiovascular disease, researchers and clinicians are seeking viable cell sources and novel cell delivery platforms that allow for replacement of diseased tissue and engraftment of new cardiomyocytes from a readily available in vitro source.

Human adult CMs are difficult to obtain for experimentation and are desired for myocardial repair in the adult patient for better mechanical and electrical integration, the process of human CM maturation is not studied yet but will provide important insights about adolescence and how the human heart remodels after birth, as well as provide more physiologically relevant features for toxicology screening and disease modeling of the adult human myocardium.

Engineered tissues that mimic aspects of human heart development can provide insight into the parameters guiding normal human cardiac development, as well as enable investigation of the mechanisms by which known teratogens disrupt this process. Although congenital heart defects are the most common type of birth defect, the causal mechanisms are still not clearly understood and human teratogens do not necessarily cause defects in animal models. Initially, human PSC (hPSC) differentiation protocols used 3D hPSC aggregation to create embryoid bodies (EBs), which replicated the cardiac developmental steps in part through the EB's spherical 3D structure. Ultimately for tissue engineering to reach its potential as a source of human heart tissue for these applications, engineered cardiac tissues must have structural and functional properties reflective of the native, mature human myocardium. Reaching this goal, however, has proven elusive.

However, to overcome the issues of inefficient cardiomyocyte (CM) production and reproducibility using EB cardiac differentiation, researchers have focused more recently on modulating the chemical environment of the differentiating stem cells; through the addition of soluble factors, this approach strives to replicate the cues directing native heart development. By utilizing 2D monolayers and the timed introduction of small molecules, highly efficient differentiation protocols have revolutionized CM production from hPSCs.

The development of methods that reduce the number of cell handling steps would facilitate the successful utilization of engineered human cardiac tissues for high throughput pharmaceutical screening and generation of mature stem cell derived cardiomyocytes (SC-CMs). To create engineered human cardiac tissues, historically, hPSCs have been first differentiated into contracting SC-CMs; these SC CMs have then been dissociated, combined with a biomaterial and additional supporting cardiac cell types, and re-assembled into cardiac tissues. In particular, this approach not only limits the direct production of mature cardiac tissues, but also hinders the ability to assess the role of cellular microenvironment or pharmaceutical-induced changes during early stages of human cardiac development. In addition to the issues in processing and replicating the early steps in human cardiac development in vitro, this approach involves multiple cell handling steps, disrupts important cell-cell junctions, and causes high degree of cell loss.

Hybrid biomaterials, like PEG-fibrinogen, have tunable mechanical properties which provide advantage over natural or synthetic materials due to the fact that matrix stiffness plays a significant role throughout cardiac differentiation but still needs to support cell survival, proliferation, and differentiation. Currently, natural biomaterials (e.g. fibrin, gelatin, collagen Type I) have been used post-differentiation for CM encapsulation to enhance cardiac tissue formation (including CM maturation and alignment), but present limitations due to their natural batch-to-batch variability, lack of immediate structural support, and long-term maintenance of spontaneous contractility in vitro. In comparison, synthetic materials are completely defined, rapidly crosslinkable with tunable properties but lack any biological component.

There exists a need for the creation of engineered tissue as models, including models of the developing human heart using PSCs. Such models will be useful for toxicity and/or efficacy of chemicals, compounds, and drugs, including, for example characterization of the response to the known cardiac teratogen thalidomide. Further, there is a need for providing a quicker, more efficient, and cost-savings methods for producing differentiated tissue in a three dimensional form.

The compositions and methods of the present invention provide for quicker, more efficient, and cost-saving production of differentiated tissue in a three dimensional form. The compositions and methods of the present invention for the growth and differentiation of stem cells are useful for treating disorders related to or benefiting from tissue regeneration. The compositions and methods of the present invention for the growth and differentiation of stem cells are also useful for screening of new or candidate compounds for efficacy, toxicity, or other activities. The methods and compositions of the present invention further provide viable cell sources and novel cell delivery platforms that allow for replacement of diseased tissue and engraftment of new cardiomyocytes from a readily available in vitro source. The methods and compositions of the present invention further provide the ability to recapitulate 3D human heart development in vitro using tissue engineered approach/reference to development toxicity screening Other objects, advantages and features of the present invention will become apparent from the following specification taken in conjunction with the accompanying drawings.

SUMMARY OF THE INVENTION

The present invention relates to compositions and methods for culturing and differentiating pluripotent stem cells into cultures or tissues in three-dimensional form. According to the invention, Applicants have developed systems and methods for direct differentiation of PSCs within a three-dimensional (3D) microenvironment created by PEG-fibrinogen hydrogels, thereby directly creating a 3D architecture without additional cell handling steps. These systems and methods allow for production of cells and tissues having characteristics not otherwise observed in cultured cells or other cells not taken directly from the corresponding tissues in the body. Using these systems and methods, PSCs encapsulated in a 3D microenvironment formed by a biomimetic material survive and degrade the biomimetic material to form compact tissues of interconnected cells over time. In one embodiment, the methods are used for cardiac regeneration, wherein PSCs undergo direct cardiac differentiation, which results in synchronously contracting cardiac tissues, including in particular 3D cardiac tissues. This differentiation of PSCs post-encapsulation to create cardiac tissues achieves CM yield as well as cardiac and functional gene expression, and calcium handling properties, which are comparable to the control 2D monolayer differentiation; with the advantage that these cardiac tissues retained their spontaneous contractile function for several months while developing ultrastructural features of mature CMs. These properties of the tissues and cultures of the present invention are previously unseen in cardiomyocytes derived from stem cells or cells not isolated from hearts In one aspect, the invention provides methods of producing three-dimensional cell cultures or tissues comprising combining a population of pluripotent stem cells (PSCs) with a biomimetic material to form a biomimetic-PSC suspension; treating said biomimetic-PSC suspension to produce a three-dimensional biomimetic-PSC microenvironment; and culturing said biomimetic-PSC microenvironment to expand in a pluripotent-state and/or to differentiate the PSCs into at least one type of somatic cell. In a further aspect, the biomimetic material can be a hydrogel. In a further aspect, the hydrogel can be a covalently linkable hydrogel. In yet a further aspect the covalently-linkable hydrogel can be a PEG-based hydrogel, such as PEG-fibrinogen.

In another aspect, the treatment of the biometric-PSC suspension to produce a three-dimensional microenvironment can involve placing said biomimetic-PSC suspension into a mold to generate a particular shape or structure of the microenvironment. Whether through use of a mold or not, the shape or structure of the microenvironment can be, for example, a microisland, cardiac disc, string, macrotissue, or microsphere. All of these can be readily dissociated to yield single cells. In a further aspect, the generation of the three-dimensional biomimetic-PSC microenvironment can be through covalently cross-linking the biomimetic material, for example, by photo-cross-linking. In one exemplary embodiment, the biomimetic material comprises PEG-fibrinogen, triethanolamine (TEOA), N-vinylpyrrolidone (NVP), and a photoinitiator such as Irgacure 2959, Irgacure 651, or Eosin Y, which produces the three-dimensional microenvironment through photo-crosslinking.

In another aspect, the methods and compositions use PSC for the generation of three dimensional cultures and tissues. In one exemplary embodiment, the PSCs are human induced PSCs (hiPSCs). The PSC can be differentiated into a variety of cell types and tissues, including cardiomyocytes and synchronously contracting, functional cardiac tissue from said cardiomyocytes.

In another aspect, the present invention provides three-dimensional cell cultures or tissues comprising differentiated somatic cells derived from pluripotent stem cells and a three-dimensional microenvironment comprising a biomimetic material. The differentiated somatic cells can be a variety of cell or tissue types, including cardiomyocytes and synchronously contracting, functional cardiac tissue.

In another aspect, the biomimetic material of the three-dimensional cell culture or tissue can be a hydrogel composed of polymeric subunits such as PEG-fibrinogen. The three-dimensional microenvironment can have a variety of shapes or structures including microislands, cardiac discs, strings, macrotissues, and microspheres.

In a further aspect the invention provides three-dimensional cell culture or tissue produced by the above methods, including differentiated cardiomyocytes and synchronously contracting, functional cardiac tissue.

In another aspect, the invention provides methods of treating an individual comprising providing a population of pluripotent stem cells (PSCs) derived from said individual, generating a three-dimensional culture or tissue from the PSCs, and providing the tissue or cell culture to the individual.

In another aspect, the invention provides kits for generating three-dimensional cell cultures or tissues, comprising a biomimetic material, such as PEG-fibrinogen, triethanolamine (TEOA), N-vinylpyrrolidone (NVP), and a photoinitiator such as Irgacure 2959, Irgacure 651, or Eosin Y; a photo cross-linking activation apparatus; and culture media formulated for differentiation of pluripotent stem cells (PSCs) into a somatic cell or tissue.

In a further aspect of the present invention, systems and methods for screening candidate compounds or substances using the three-dimensional cultures and tissues are provided.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DESCRIPTION OF THE FIGURES

FIG. 4 (a-e) shows increased pacing frequencies and isoproterenol addition decreased calcium transient time to baseline of 2D and 3D cultured cells. Calcium transient analysis of 14 day old 3D cultured CMs and age-matched control 2D monolayers. Time to baseline (t to b1) (a) 50% and (b) 80% did not show significant differences between 2D and 3D cultured CMs. (c) Representative calcium transient traces of 2D and 3D cultured cells. (d) Addition of isoproterenol significantly shortened calcium transient t to b1 50% and 80% of spontaneously contracting 3D cultured CMs and (e) increased spontaneous beating rate. n=3. P<0.05, * vs. Pre-Isoproterenol.

FIG. 12 (a-h) shows that initial cell-seeding density can be varied to produce contracting cardiac tissues. Original cell seeding density (60 million/ml) and (e-h) 50% of original cell seeding density (30 million/ml) was compared during early stages of tissue formation. Increase in cell number (darkening effect) over time was observed for both cell seeding densities.

Figure 1A:
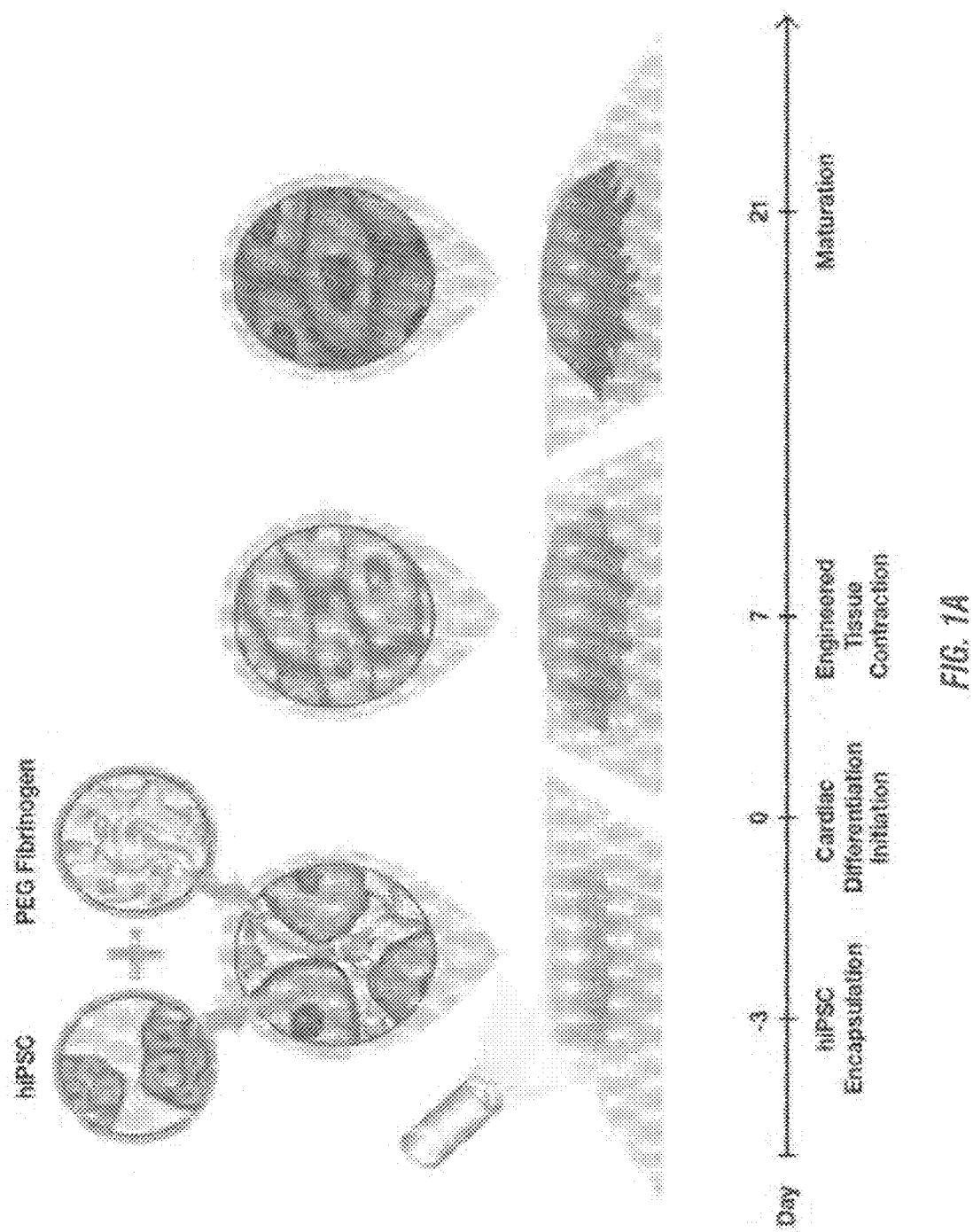
FIG. 1 (a-k) shows a schematic and progression of hiPSC encapsulation to produce 3D cardiac microislands. (a) HIPSCs are combined with liquid PEG-fibrinogen precursor, added into a PDMS mold (not shown) on acrylated glass, and photocrosslinked under visible light to form microislands. All encapsulated hiPSCs are maintained in their pluripotent state for three days, followed by induction of cardiac differentiation to produce uniform contracting, cardiac tissues. Encapsulated (b) clump and (h) single hiPSCs form uniform microislands (images taken on day 0 of differentiation), where (c, d and i, j) hiPSCs remain viable 24 hours post-encapsulation and (e-g, k-m) proliferate during early stages of cardiac differentiation.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art. The methods and techniques are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol. 1, CRC Press (1976); Handbook of Biochemistry: Section A Proteins, Vol. 11, CRC Press (1976); Essentials of Glycobiology, Cold Spring Harbor Laboratory Press (1999), which are incorporated herein by reference.

The following terms, unless otherwise indicated, shall be understood to have the following meanings:

The articles "a" and "an" are used herein to refer to one or to more than one (i.e., to at least one) of the grammatical object of the article. By way of example, "an element" means one element or more than one element.

By the term "applicator" as the term is used herein, is meant any device including, but not limited to, a hypodermic syringe, a pipette, a bronchoscope, a nebulizer, and the like, for administering a composition of the invention to a mammal.

"Biomimetic materials" refers to materials which act to emulate properties from a natural biological environment. Such materials may be selected based on one or more characteristics, including, for example, ability to maintain the mechanical and electrical properties of the native tissue, direct cell and tissue orientation, deliver particular drugs and growth factors, and degrade in response to enzymes secreted by cells. Furthermore, these materials can be selected based on ability to promote cell adhesion, mechanical stretch and electrical conduction. Overall, biomimetic materials can be engineered or selected to produce functional tissue with highly controlled, defined properties. Examples of biomimetic materials include natural materials and synthetic materials. Natural materials include, but are not limited to, materials derived from proteins, polysaccharides, and other derivatives of these substances, such as, for example, collagen, gelatin, glycosaminoglycans (e.g. hyaluronic acid), elastin, fibronectin, laminin, fibrin, and alginates. Synthetic materials include temporally-changing or externally-modifiable materials that can be engineered to provide biomimetic properties that facilitate cardiac regeneration. Materials that fall into this category are unique in their ability to change structure based on changes in input (temperature, pH, photoactive, mechanical/electrical stress hydrogels, environmentally-responsive polymers, and conductive materials.

The term "crosslink" refers to a bond or chain of atoms attached between and linking two different polymer chains.

A "defined culture medium" as the term is used herein refers to a cell culture medium with a known composition.

As the term is used herein, a cell is said to be "eliminated" from a population of cells, or from a culture medium, when the cell no longer exerts one or more of a physical, biological or chemical effect on the population of cells or culture medium. For example, a cell may be eliminated from a culture medium by physically removing the cell using FACS or by using an antibody specific for a cell surface marker unique to that cell. A cell may also be eliminated from a culture medium by rendering the biological activity of that cell inert, such as, for example, by using a neutralizing antibody that is specific for that cell.

A cell is "essentially eliminated" from a population of cells, or from a culture medium, when most, but not all of the total number of such cells no longer exerts one or more of a physical, biological or chemical effect on the population of cells or culture medium. For example, a particular type of cell may be essentially eliminated from a culture medium if at least 75% of the cells of that type are removed from the culture medium by using an antibody specific for a cell surface marker unique to that cell. More preferably, at least 80% of the cells are eliminated from the culture medium, even more preferably, at least 85%, more preferably, at least 90%, and even more preferably, at least 95% of the cells are eliminated from the culture medium.

"Enriching," as the term is used herein, refers to the process by which the concentration, number, or activity of something is increased from a prior state. For example, a population of 100 PSCs is considered to be "enriched" in hiPSCs if the population previously contained only 50 PSCs. Similarly, a population of 100 PSCs is also considered to be "enriched" in PSCs if the population previously contained 99 PSCs. Likewise, a population of 100 PSCs is also considered to be "enriched" in PSCs even if the population previously contained zero PSCs.

The term "hydrogel" refers to a water-swellable polymeric matrix, consisting of a three-dimensional network of macromolecules held together by covalent crosslinks that can absorb a substantial amount of water to form an elastic gel.

As the term is used herein, "isolated" refers to a polynucleotide, polypeptide, protein, molecule, compound, material or cell of genomic or synthetic origin or some combination thereof which is not associated with all or a portion of the polynucleotides, polypeptides, proteins, molecules, compounds, materials or cells with which the isolated polynucleotide, polypeptide, protein, molecule, compound, material or cell is found in nature, or is linked to a polynucleotide, polypeptide, protein, molecule, compound, material or cell to which it is not linked in nature.

"Maintenance" of a cell or a population of cells refers to the condition in which a living cell or living cell population is neither increasing nor decreasing in total number of cells in a culture. Alternatively, "proliferation" of a cell or population of cells, as the term is used herein, refers to the condition in which the number of living cells increases as a function of time with respect to the original number of cells in the culture.

The term "PEG" as used herein refers to poly(ethylene glycol).

The phrase "pluripotent stem cells" (PSCs) refers to stem cells that have the potential to differentiate into any of the three germ layers: endoderm (interior stomach lining, gastrointestinal tract, the lungs), mesoderm (muscle, bone, blood, urogenital), or ectoderm (epidermal tissues and nervous system). PSCs of the present invention include embryonic PSCs and induced PSCs, which are derived from a non-pluripotent cell, typically an adult somatic cell, generated by any method known in the art, including, for example, through introduction or activation of specific transcription factors and/or genes.

As the term is used herein, "population" refers to two or more cells.

A "somatic cell" is understood to be a biological cell ordinarily found in a multicellular organism that is not a gamete, germ cell, gametocyte, or undifferentiated stem cell. Somatic cells include cells of the endoderm (interior stomach lining, gastrointestinal tract, the lungs), mesoderm (muscle, bone, blood, urogenital), and ectoderm (epidermal tissues and nervous system).

"Substantially homogeneous," as the term is used herein, refers to a population of a substance that is comprised primarily of that substance, and one in which impurities have been minimized.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances.

In one aspect, a first substance is substantially separated from a second substance if the ratio of the concentration of the first substance to the concentration of the second substance is greater than about 1. In another aspect, a first substance is substantially separated from a second substance if the ratio of the concentration of the first substance to the concentration of the second substance is greater than about 2. In yet another aspect, a first substance is substantially separated from a second substance if the ratio of the concentration of the first substance to the concentration of the second substance is greater than about 5. In another aspect, a first substance is substantially separated from a second substance if the ratio of the concentration of the first substance to the concentration of the second substance is greater than about 10. In still another aspect, a first substance is substantially separated from a second substance if the ratio of the concentration of the first substance to the concentration of the second substance is greater than about 50. In another aspect, a first substance is substantially separated from a second substance if the ratio of the concentration of the first substance to the concentration of the second substance is greater than about 100. In still another aspect, a first substance is substantially separated from a second substance if there is no detectable level of the second substance in the composition containing the first substance.

Pluripotent Stem Cell Culture Systems

In one aspect, the present invention provides systems for generating three-dimensional cell cultures or tissues. The systems can include one or more biomimetic materials, culture media, and a stem cell population. The biomimetic material can be selected based on a number of factors, including the type of cell or tissue to be obtained. Pluripotent stem cells (PSCs) suitable for the differentiation methods disclosed herein include, but are not limited to, embryonic stem cells, including human embryonic stem cells (hESCs), human induced pluripotent stem cells (hiPSCs), non-human primate embryonic stem cells (nhpESCs), non-human primate induced pluripotent stem cells (nhpiPSCs). In another aspect, the systems may include a photo cross-linking activation apparatus. In another aspect, the culture media can be formulated for differentiation of pluripotent stein cells (PSCs) into a somatic cell or tissue, including, for example, cardiomyocytes or cardiac tissue, and neural cells and tissue.

Biomimetic Materials and Hydrogels

Figure 7A:
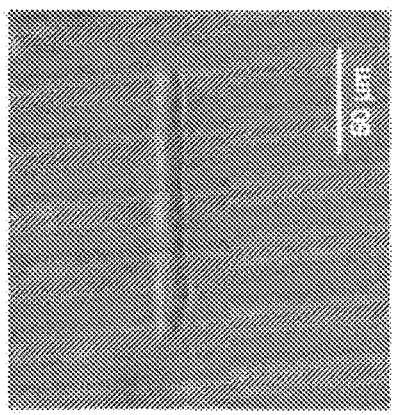
FIG. 7 (a-e) shows a one-step encapsulation approach according to an exemplary embodiment of the invention that is applicable for a wide range of tissue sizes and geometries. Uniform contracting tissues, in addition to (a) microislands, can take place on a variety of platforms including: (b) macrotissues, (c) microspheres, or (d) tissue-dissociated single cells. (e) Tissue sizes and geometries depend on desired future applications, e.g. production of microislands or macrodiscs for drug testing, macrotissues for mechanical testing, microspheres for injectable scaffolds, or single cells post-tissue digestion for automated patch clamping.
Figure 7B:
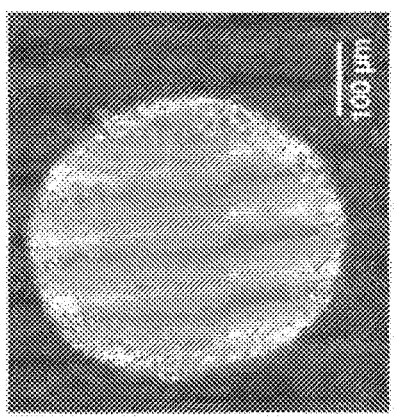
Figure 7C:
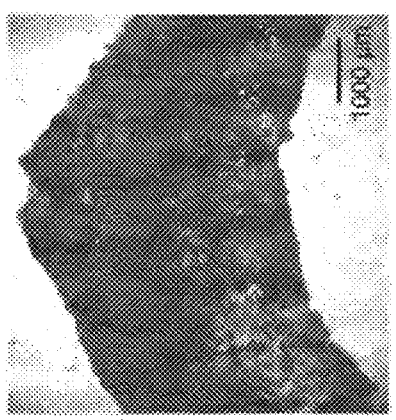
Figure 7D:
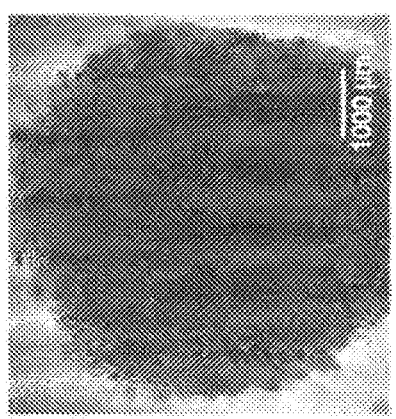
Figure 7E:
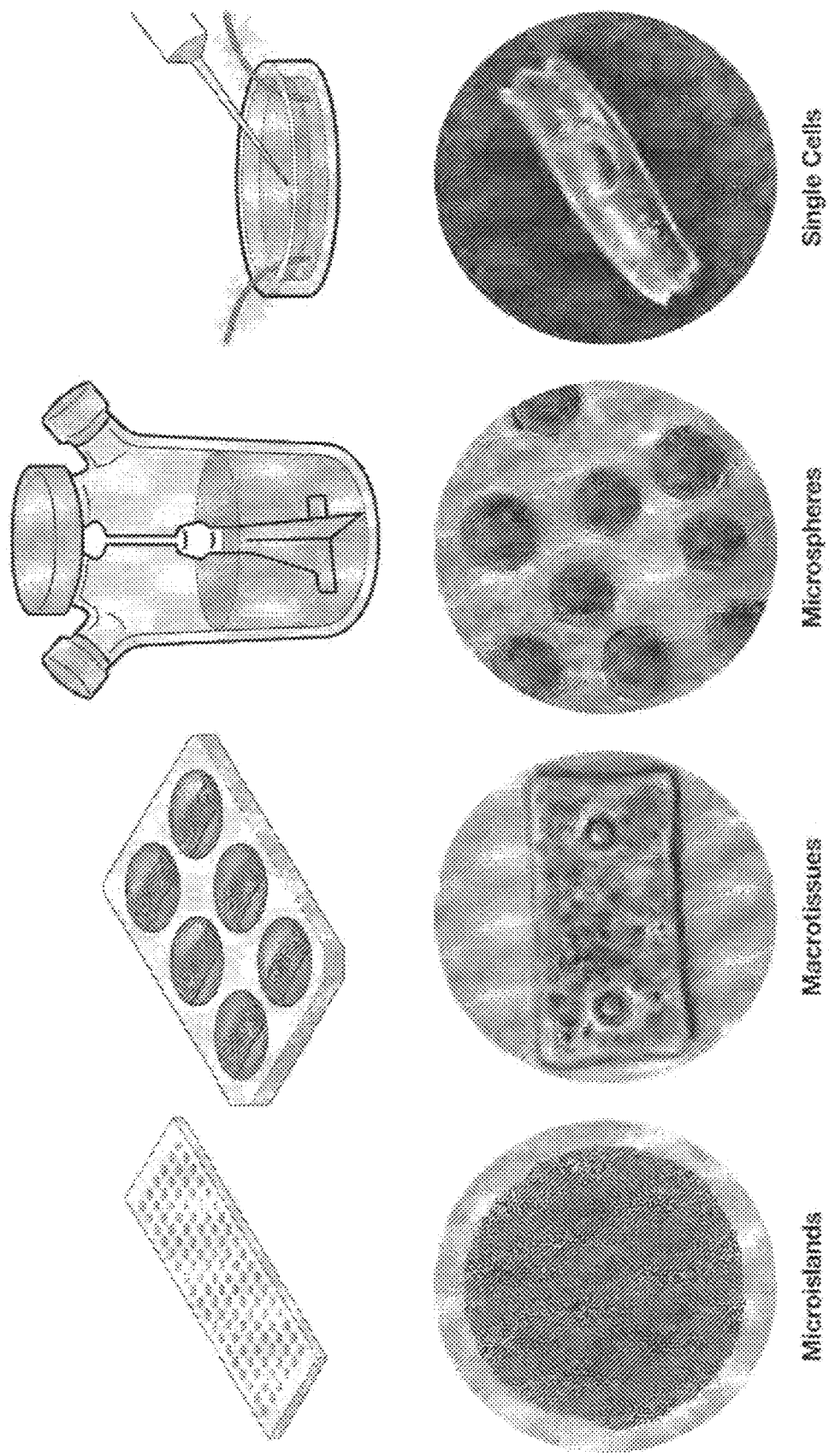

According to one aspect of the invention, systems and methods for culturing and differentiating pluripotent stein cells include biomimetic materials as microenvironment, structure, or architecture within which PSCs can grow and differentiate. Biomimetic materials for use in the present invention include biomaterials that can be engineered or selected to produce functional tissue with highly controlled, defined properties. Examples of biomimetic materials include natural materials and synthetic materials, or a combination of natural materials and synthetic materials. Examples of biomaterials can be found in U.S. Pat. No. 8,691,276, titled "Extracellular matrix-derived gels and related methods" which is incorporated herein in its entirety. Natural materials include, but are not limited to, materials derived from proteins, polysaccharides, and other derivatives of these substances, such as, for example, collagen, gelatin, glycosaminoglycans (e.g. hyaluronic acid), elastin, fibronectin, laminin, fibrin, and alginates. Synthetic materials include temporally-changing or externally-modifiable materials that can be engineered to provide biomimetic properties that facilitate cardiac regeneration. Examples of synthetic biomimetic materials include, but are not limited to, polycaprolactone (PCL), poly(glycolic acid) (PGA), poly-4-hydroxybutyrate (P4HB), poly (lactic acid) (PLA) and poly(lactic-co-glycolic acid) (PLGA), poly(glycerol-sebacate) (PGS) (FIG. 7(d)), poly(trimethylene carbonate-co-lactide), polyester urethane urea (PEUU)129 and poly-urethane; and copolymers of natural and synthetic materials. Materials that fall into this category are unique in their ability to change structure based on changes in input (temperature, pH, photoactive, mechanical/electrical stress hydrogels, environmentally-responsive polymers, and conductive materials).

An exemplary natural or synthetic biomimetic material includes hydrogels. Hydrogels are insoluble, cross-linked polymer network structures composed of hydrophilic homo- or hetero-co-polymers, which have the ability to absorb significant amounts of water. Consequently, this is an essential property to achieve an immunotolerant surface and matrix (i.e., with respect to protein adsorption or cell adhesion). Due to their significant water content, hydrogels also possess a degree of flexibility very similar to natural tissue, which minimizes potential irritation to surrounding membranes and tissues. In general, hydrogels are strong hydrophiles, capable of supporting nutrient transport and controlled degradation to allow for cell proliferation, generally composed of self-assembling materials, namely peptide amphiphiles. Hydrogels are highly absorbent (they can contain over 90% water) natural or synthetic polymeric networks. Hydrogels also possess a degree of flexibility very similar to natural tissue, due to their significant water content. Hydrogels for use in the present invention include both entangled hydrogels and covalently linkable hydrogels. In a further aspect, covalently-linkable hydrogels are used as the biomimetic material based on advantageous characteristic, including, for example, the ability to reproducibly form three-dimensional structures using molds or deposition techniques. Covalently-linkable hydrogels include all aqueous-based covalently-linkable hydrogels, including all hydrogels formed from natural polymers and hydrogels formed from synthetic polymers. Covalently linkable hydrogels also include PEG-based (polyethylene glycol) and non-PEG-based polymers; non-PEG-based hydrogels include both natural and synthetic hydrogels. In a most particular aspect, hydrogels of the present invention can be composed of PEGylated fibrinogen, where the naturally occurring component fibrinogen is directly coupled to acrylated PEG to form PEG-fibrinogen. In another aspect, the biomimetic material of the present invention can be an acrylated gelatin.

In one aspect, the methods of the present invention for producing 3D cultures or tissues can include modulation of the mechanical properties of a hydrogel for different types of cells and/or tissues. In addition, the methods can use state-of-the-art soluble factors and/or media formulations to drive formation of a variety of somatic cells and tissues. In one aspect, the methods can be used to generate cardiac cells or tissues. In another aspect, for example, the methods can be used to generate neural tissue formation, using similar PEG-fibrinogen crosslinking density and/or mechanical properties as those used for production of cardiac cells and tissues, but different soluble factors and media formulation. The density and crosslinking properties of PEG-fibrinogen can be varied by one or more of the following: crosslinking time/light intensity, concentration of PEG-fibrinogen, inclusion of a porogen (e.g. gelatin beads), or addition of 1% or 2% PEG-diacrylate (with or without a matrix metalloproteinase degradable peptide segment, such as acryl-PEG-degradable_peptide-PEG-acryl).

For clarity, PEG fibrin has also previously been described for use as a biomimetic material, PEG fibrin differs from PEG-fibrinogen in several ways, including that the PEG group is not coupled to the fibrin molecule; as a result the PEG fibrin properties differ substantially from those of PEG-fibrinogen, including mechanical properties, such as resistance to compaction by incorporated cells. PEG fibrin materials are also hydrogels as described above, but are not the same material as PEG-fibrinogen. PEG-fibrinogen and PEG-fibrinogen hydrogels are described, for example in U.S. Pat. No. 8,858,925, titled "Pegylated fibrinogen precursor molecule" issued Oct. 14, 2014. Generally, PEG-fibrinogen is a preferred biomimetic material for formation of three-dimensional microenvironments due to its beneficial characteristics, including structural characteristics of synthetic materials and biofunctionality of natural materials; biodegradability, and capability of forming three-dimensional structures through covalent crosslinking, including by photo-crosslinking.

Photo-Crosslinking

In one aspect, the invention involves the formation of 3D microenvironments by treating a suspension of PSCs and a biomimetic material. The treating cross-links the biomimetic material to form a 3D structure, which may be determined by the use of a mold or by deposition on a substrate. The cross-linking may be through any of a variety of covalent bonding reactions, including, for example, activation reactions, reduction-oxidation (redox) reactions, and Lewis acid-base reactions. In an exemplary embodiment, the cross-linking is accomplished by photo-crosslinking or photopolymerization. For creation of 3D microenvironments by photo-crosslinking, the biomimetic material may comprise PEG-fibrinogen, an accelerator, and at least one initiator or photoinitiator component. In an exemplary embodiment, the accelerator may be N-vinylpyrrolidone (NVP), and the initiator or photoinitiator component may be triethanolamine (TEOA) and/or Eosin Y. Stimulating the cross-linking reaction by exposing the mixture of biomimetic material, accelerator, and one or more initiator or photoinitiator components to a particular wavelength and intensity of light produces the three-dimensional microenvironment through photo-crosslinking. The light required for photo-crosslinking may be supplied by a photo-crosslinking activation apparatus.

Accelerators for use in cross-linking biomimetic materials include, but are not limited to, tetraethylmethylenediamine (TEMED), N,N,N,N-tetramethylethylenediamine (TMEDAN), sodium bisulphatem, sodium metasulphitand-vinylpyrrolidone (NVP).

Photoinitiator components for use in photo-crosslinking include, but are not limited to, bis(2,4,6-trimethylbenzoyl) phenylphosphine oxide (BAPO), 2,2-dimethoxy-2-phenyl-lacetophenone (DMPA), camphorquinone (CQ), 1-phenyl-1,2-propanedione (PPD), the organometallic complex Cp'Pt (CH(3))(3) (Cp'=eta(5)-C(5)H(4)CH(3,2-hydroxy-1,4-(hydroxyethoxy)phenyl]-2-methyl-1-propanone (Irgacure 2959), dimethylaminoethyl methacrylate (DMAEMA), 2,2-dimethoxy-2-phenylacetophenone, benzophenone (BP), Flavin, triethanolamine (TEOA), and Eosin Y.

The photoinitiation reaction can be performed using a variety of wave-lengths including UV (190-365 nm) wave-lengths, and visible light (400-1100 nm) and at various light intensities. It will be appreciated that for ex vivo or in vivo applications, the photoinitiator and wavelengths used are preferably non-toxic and/or non-hazardous.

A photo-cross-linking activation apparatus of the present invention includes any device capable of producing electro-magnetic energy of an appropriate wavelength and sufficient intensity to initiate photopolymerization. The apparatus can generate ultraviolet radiation, i.e., radiation having a wave-length shorter than 400 nm, and usually from mercury lamps, for example mercury resonance lamps with output at 313 nm and 364 nm. The apparatus can also be a laser generator. The apparatus can also produce visible light. The apparatus can be any commercially available device. In an exemplary embodiment, the apparatus produces visible (non-UV) light at an intensity of 48 mW/cm$^2$ at a distance 3 cm away.

PSC Differentiation

PSCs derived from an individual can be produced by any methods known in the art. For example, methods of generating PSCs from mammalian somatic cells are described in U.S. Pat. No. 8,808,982, titled "Compositions and methods for reprogramming eukaryotic cells" which issued Aug. 19, 2014; U.S. Pat. No. 8,673,633, titled "Method for producing induced pluripotent stem cells with high efficiency and induced pluripotent stem cells produced thereby" which issued Mar. 18, 2014; and U.S. Pat. No. 8,278,104 titled "Induced pluripotent stem cells produced with Oct3/4, Klf4 and Sox2" issued Oct. 2, 2012, all of which are incorporated herein in their entirety.

Other suitable human embryonic stein (ES) cells for use in the present invention include, but are not limited to, any of a variety of available human ES lines, e.g., BG01 (hES-BGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ESO4 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

PSCs can be differentiated into a variety of somatic cells, including endoderm (interior stomach lining, gastrointestinal tract, the lungs), mesoderm (muscle, bone, blood, urogenital), or ectoderm (epidermal tissues and nervous system) cells, depending on a number of culturing conditions. Conditions that may be varied include, for example, the type of biomimetic material used, the shape of the three-dimensional microenvironment, the type and amount of growth factors supplied to the PSCs, and the time of culture. Media and conditions for differentiation of PSC, including hiPSCs, into various somatic cells are known in the art. The particular media, growth factors, and other culture conditions can be selected in order to produce a desired cell type.

In an exemplary embodiment, PSCs associated with the three-dimensional microenvironment can be differentiated into cardiomyocytes or cardiac tissue. In a specific exemplary embodiment, PSCs are differentiated into cardiomyocytes by the following protocol: On day 0 of differentiation, media was changed from mTeSR-1 to 2 ml RPMI/B27 without insulin+12 µM CHIR99021 media per well. After 24 h (day 1), media was changed to 2 ml RPMI/B27 without insulin. On day 3 of differentiation, media was replaced with 1 ml fresh RPMI/B27 without insulin, 5 µM IWP2, and 1 ml old RPMI/B27 without insulin and cultured for an additional 48 h. On day 5, media was switched back to 2 ml RPMI/B27 without insulin and followed by 2 ml RPMI/B27 media on day 7, media being replaced thereafter every three days.

Methods of Producing Three-Dimensional Cultures and Tissues

In one aspect, the invention provides methods of producing three-dimensional cell cultures or tissues comprising combining a population of pluripotent stem cells (PSCs) with a biomimetic material to form a biomimetic-PSC suspension; treating said biomimetic-PSC suspension to produce a three-dimensional biomimetic-PSC microenvironment; and culturing said biomimetic-PSC microenvironment to expand their pluripotent state and then to differentiated the PSCs into at least one type of somatic cell. In a further aspect, the biomimetic material can be a hydrogel. In a further aspect, the hydrogel can be a covalently linkable hydrogel. In yet a further aspect the covalently-linkable hydrogel can be a PEG-based hydrogel, such as PEG-fibrinogen.

In another aspect, the treatment of the biomimetic-PSC suspension to produce a three-dimensional microenvironment can involve placing said biomimetic-PSC suspension into a mold to generate a particular shape or structure of the microenvironment. Whether through use of a mold or not, the shape or structure of the microenvironment can be, for example, a microisland, cardiac disc, string, macrotissue, or microsphere. In a further aspect, the generation of the three-dimensional biomimetic-PSC microenvironment can be through covalently cross-linking the biomimetic material, for example, by photo-cross-linking. In one exemplary embodiment, the biomimetic material comprises PEG-fibrinogen, an accelerator, such as N-vinylpyrrolidone (NVP), and at least one initiator or photoinitiator component, such as triethanolamine (TEOA), and Eosin Y. Stimulating the cross-linking reaction by exposing the mixture of biomimetic material, accelerator, and one or more initiator or photoinitiator components to a particular wavelength and intensity of light produces the three-dimensional microenvironment through photo-crosslinking.

In another aspect, the methods and compositions use PSC for the generation of three dimensional cultures and tissues. In one exemplary embodiment, the PSCs are human induced PSCs (hiPSCs). The PSC can be differentiated into a variety of cell types and tissues, including cardiomyocytes and synchronously contracting, functional cardiac tissue from said cardiomyocytes.

In an exemplary embodiment, the method of producing three-dimensional culture or tissue comprises culturing hiPSCs on Matrigel in mTeSR-1 media. Collecting hiPSCs, centrifuging, and resuspending in PEG-Fb precursor solution comprising PEG-Fb, triethanolamine (TEOA), N-vinylpyrrolidone (NVP), and the photoinitiator Eosin Y; transferring the cell-PEG-Fb suspension to a polydimethylsiloxane (PDMS) mold and photocrosslinking using visible light exposure to form tissues; culturing tissues in mTeSR-1 media for three days followed by initiation of differentiation.

In one aspect, methods of the present invention involve association of PSCs with a biomimetic material. The association of the cells with the biomimetic material can be deposition of the cells onto a matrix composed of the biomimetic material or encapsulation of the cells within a structure composed of the biomimetic material. The cells and associated biomimetic material can be formed into various shapes or orientations depending on the desired characteristics and/or type of cells or tissue to be produced. A desired shape can be obtained by various means, depending on the type of biomimetic material used, including for example covalent cross-linking, photo-cross-linking, suspension in media, immobilization or deposition on a substrate, printing, and/or molding. Examples of shapes and orientations for generation of three-dimensional cultures and tissues include but are not limited to, microislands, cardiac discs, strings, macrotissues, and microspheres, and by dissociation thereof, single cells.

In one aspect, the methods of the present invention involve treating a suspension of PSC and a biomimetic material to produce a three-dimensional microenvironment. In one embodiment, the treatment cross-links the biomimetic material, for example by covalently linking the biomimetic material components. As understood by one of skill in the art, covalent cross-linking of biomimetic materials, including for example hydrogels such as PEG-fibrinogen, can be accomplished by a variety of different methods. For example, the biomimetic material may be photo-cross-linked (also known as "photopolymerized"). Photopolymerization and photo-cross-linking are described, for example, in U.S. Pat. No. 5,137,800, titled "Production of three dimensional bodies by photopolymerization" issued Aug. 11, 1992. Generally, a body of a composition (i.e. a suspension) comprising a photopolymerizable monomer, such as an acrylate or an acrylate derivative or PEG-fibrinogen, a "photoinitiator", and, usually, an "accelerator" are caused to undergo photopolymerization by subjecting the composition to activating radiation of a suitable wave length. Activating radiation causes the photoinitiator to undergo a reaction, producing an intermediate which includes a free radical chain and, as a consequence, causes the monomer to polymerize.

In one aspect, the methods of the present invention involve differentiation of PSCs into somatic cells. PSCs can be differentiated into a variety of somatic cells, including endoderm (interior stomach lining, gastrointestinal tract, the lungs), mesoderm (muscle, bone, blood, urogenital), or ectoderm (epidermal tissues and nervous system) cells, depending on a number of culturing conditions. Conditions that may be varied include, for example, the type of biomimetic material used, the shape of the three-dimensional microenvironment, the type and amount of growth factors supplied to the PSCs, and the time of culture.

In one embodiment, the methods involve the differentiation of PSCs into cardiac cells or cardiac tissue. In another embodiment, the methods involve the differentiation of PSCs into neural cells, including neural stem cells (NSCs) that are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. In another embodiment, the methods involve differentiation of PSCs into insulin-producing cells or hematopoietic stem cells.

Three-Dimensional Cell Cultures and Tissues

In another aspect, the present invention provides three-dimensional cell cultures or tissues comprising differentiated somatic cells derived from pluripotent stem cells and a three-dimensional microenvironment comprising a biomimetic material. The differentiated somatic cells can be a variety of cell or tissue types, including cardiomyocytes and synchronously contracting, functional cardiac tissue.

In another aspect, the biomimetic material of the three-dimensional cell culture or tissue can be a hydrogel composed of polymeric subunits such as PEG-fibrinogen. The three-dimensional microenvironment can have a variety of shapes or structures including single cells, microislands, cardiac discs, strings, macrotissues, and microspheres.

Three-dimensional cell cultures and tissues of the present invention exhibit advantageous characteristics compared to two-dimensional cell cultures and tissues produced by other methods. For example, three-dimensional differentiated and cultured SC-CMs present sarcomere spacing of $1.9 \pm 0.1$ μm, similar to mature CMs. Furthermore, ultrastructural features of mature CMs were identified on day 124 of culture. As opposed to other culture methods where no T tubule formation has ever been detected in SC CMs, T-tubule formation and other mature ultrastructural features that are important in contraction excitation coupling have been detected in these three-dimensional differentiated and cultured CMs due to the continuous three-dimensional microenvironment that allowed cells to secrete their own ECM proteins. Further, increased beating rates of spontaneously contracting three-dimensional cultured CMs in response to isoproterenol indicate that β-adrenergic signaling is operational in early stage CMs.

In a further aspect the invention provides three-dimensional cell culture or tissue produced by the above methods, including differentiated cardiomyocytes and synchronously contracting, functional cardiac tissue.

Screening and Treatment Methods

In another aspect, the invention provides methods of treating an individual comprising providing a population of pluripotent stem cells (PSCs) derived from said individual, generating a three-dimensional culture or tissue from the PSCs, and providing the tissue or cell culture to the individual. PSCs derived from an individual can be produced by any methods known in the art. For example, methods of generating PSCs from mammalian somatic cells are described in U.S. Pat. No. 8,808,982, titled "Compositions and methods for reprogramming eukaryotic cells" which issued Aug. 19, 2014; U.S. Pat. No. 8,673,633, titled "Method for producing induced pluripotent stem cells with high efficiency and induced pluripotent stem cells produced thereby" which issued Mar. 18, 2014; and U.S. Pat. No. 8,278,104 titled "Induced pluripotent stem cells produced with Oct3/4, Klf4 and Sox2" issued Oct. 2, 2012, all of which are incorporated herein in their entirety.

According to a further aspect of the invention, PSC-derived tissues and cells, and methods for producing 3D tissues and cell cultures can be used to introduce the cells or tissues into an individual for treatment of diseases. Such methods are particularly favored for treatment of diseases involving cells or tissues that are unable to be repaired by the body. For example, cardiac cells or tissues may be provided to an individual to treated a disease afflicting the cardiac system, or neural cells or tissue may be provided to an individual to treat a disease of the neural systems, including, for example, Parkinson's disease, Alzheimer disease, Huntington's disease, or to treat damage caused by, for example, traumatic injury or stroke. In other aspects, the methods involve production and provision of insulin-producing cells or hematopoietic stem cells for treatment of diseases affecting those cell types, such as for example, diabetes. In one aspect, the methods of producing 3D cell culture and tissues can be used for autologous tissue regeneration of organs and cells. In a further aspect, the methods of producing 3D cell culture and tissues can be used for treatment of genetic diseases, wherein, for example, genetic defects could be repaired prior to differentiation of PSCs. In yet a further aspect, the methods of producing 3D tissues or cell production can be used to treat patients with cardiac diseases, including, for example, Timothy-syndrome or muscular dystrophy. In a further aspect, methods for production 3D tissues or cell cultures may be used for cardiac regeneration applications including, but not limited to, repair of damage to the myocardium post-myocardial infarct, treatment of cardiomyopathy/heart failure (brought about by a range of causes), repair conducting cardiac tissues (to replace current pacemaker devices)/treatment of arrhythmias, augmentation of myocardial wall stiffness to improve valve function/slow heart disease progression/prevent heart failure, and repair of congenital heart defects. Methods for producing three-dimensional cell cultures or tissues comprise combining a population of pluripotent stem cells (PSCs) with a biomimetic material to form a biomimetic-PSC suspension; treating said biomimetic-PSC suspension to produce a three-dimensional biomimetic-PSC microenvironment; and culturing said biomimetic-PSC microenvironment to differentiate the PSCs into at least one type of somatic cell. In a further aspect, the biomimetic material can be a hydrogel, In a further aspect of the present invention, systems and methods for screening candidate compounds or substances using the three-dimensional cultures and tissues are provided. Three-dimensional cultures and tissues produced by the methods described can be exposed to a candidate compound, and thereafter the toxicity of the compound to the particular cell or tissue can be determined by assessing the cell or tissue using a variety of techniques known in the art.

Additional Embodiments

Various aspects of the present invention are illustrated in the following embodiments.

In one aspect, the present invention includes methods of producing three-dimensional cell cultures or tissues comprising combining a population of pluripotent stem cells (PSCs) with a biomimetic material to form a biomimetic-PSC suspension; treating said biomimetic-PSC suspension to produce a three-dimensional biomimetic-PSC microenvironment; and culturing said biomimetic-PSC microenvironment to differentiate the PSCs into at least one type of somatic cell. In a further aspect, the biomimetic material is a hydrogel, which can be a covalently-linkable hydrogel, such as, for example, a PEG-based hydrogel. The PEG-based hydrogel can be, for example, PEG-fibrinogen.

In another aspect, the methods of producing 3D cell cultures or tissues involve treating said biomimetic-PSC suspension BY placing said biomimetic-PSC suspension into a mold in order to impart a particular shape of structure to the resulting 3D microenvironment. The 3D microenvironment can be any number of shapes or structures, including, for example, microislands, cardiac discs, strings, macrotissues, and microspheres, and combinations thereof.

In a further aspect of the invention, formation of 3D microenvironments by treating a biomimetic-PSC suspension can be through covalently cross-linking the biomimetic material. Such covalent cross-linking can be by, for example, photo-crosslinking. Photo-cross-linking can be accomplished, for example, by formulating the biomimetic material to comprise PEG-fibrinogen, an accelerator, and at least one initiator or photoinitiator component. In one particular aspect, the accelerator is triethanolamine (TEOA), and the initiator or photoinitiator components are N-vinylpyrrolidone (NVP) and Eosin Y2.

In another aspect, the methods of producing three-dimensional cell cultures or tissues use human induced PSCs (hiPSCs). The PSCs, including hiPSCs, can be differentiated into a variety of somatic cells, including, for example, cardiomyocytes. In a more particular aspect, the methods can produce synchronously contracting, functional cardiac tissue from said cardiomyocytes.

In another aspect, the invention provides compositions of three-dimensional cell culture or tissue comprising differentiated somatic cells derived from pluripotent stem cells; and a three-dimensional microenvironment comprising a biomimetic material. In a further aspect, the somatic cells of the 3D cell culture or tissue are cardiomyocytes or cardiac tissue. In another aspect, the biomimetic material of the three-dimensional cell culture or tissue is a hydrogel, such as PEG-fibrinogen. In a further aspect the three-dimensional cell culture or tissue can be a microisland, cardiac disc, string, macrotissue, or microsphere.

In another aspect, the invention provides three-dimensional cell cultures or tissues produced by the method comprising combining a population of pluripotent stem cells (PSCs) with a biomimetic material to form a biomimetic-PSC suspension; treating said biomimetic-PSC suspension to produce a three-dimensional biomimetic-PSC microenvironment, wherein said treating covalently cross-links the biomimetic material; and culturing said biomimetic-PSC microenvironment to differentiate the PSCs into at least one type of somatic cell.

In another aspect, the invention provides methods of treating an individual comprising providing a population of pluripotent stem cells (PSCs) derived from said individual; combining the population of PSCs with a biomimetic material to form a biomimetic-PSC suspension; treating said biomimetic-PSC suspension to produce a three-dimensional biomimetic-PSC microenvironment, wherein said treating covalently cross-links the biomimetic material; culturing said biomimetic-PSC microenvironment to to differentiate the PSCs into a cell culture or tissue comprising at least one type of somatic cell; and providing the tissue, or cells from said cell culture or tissue, to said individual.

In another aspect, the invention includes kits for generating three-dimensional cell cultures or tissues, comprising a biomimetic material comprising PEG-fibrinogen, triethanolamine (TEOA), N-vinylpyrrolidone (NVP), and a photoinitiator; and culture media formulated for differentiation of pluripotent stem cells (PSCs). The kit may also include a photo-crosslinking apparatus.

In another aspect, the invention involves methods of personalized medicine for individuals having or suspected of having a disease. These methods include screening candidate compounds or substances for toxicity to cells or tissues derived from the individual comprising generating a tissue or culture comprising at least one somatic cell type by combining a population of pluripotent stem cells (PSCs) with a biomimetic material to form a biomimetic-PSC suspension; treating said biomimetic-PSC suspension to produce a three-dimensional biomimetic-PSC microenvironment; culturing said biomimetic-PSC microenvironment to differentiate the PSCs into a tissue or culture comprising at least on somatic cell type. The cells or tissue can then be exposed to a candidate compound or substance; and the toxicity of said candidate compound to the tissue or cell culture can be determined. This screening can then be used to formulate a treatment regime, for example by excluding drugs or compounds or combinations of drugs or compounds that exhibit toxicity to the cells or tissue derived from the individual. Alternatively, the cells or tissues can be used to determine sufficient or enhanced efficacy of particular drugs or compounds, which can then be administered to the individual based on the level of efficacy.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: PEG-Fibrinogen Hydrogels Support Stem Cell Survival and Proliferation HiPSC Expansion and Culture.

IMR-90 Clone 1 human induced pluripotent stem cells (hiPSCs) were purchased from WiCell and maintained at 37° C., 5% $CO_2$, and 85% relative humidity. HiPSCs were cultured as colonies on hESC qualified Matrigel (BD Biosciences) using mTeSR-1 media (Stem Cell Technologies). HiPSCs were passaged using Versene (Life Technologies) and 5 µM ROCK inhibitor (Y 27632, R&D Systems) was added to the mTeSR-1 media for 24 h post-seeding.

HiPSC viability on day −2 (24 hours post-encapsulation) was assessed using a LIVE/DEAD® viability kit (Molecular Probes) following manufacturer's instructions. Z-stacks (step size=5 µm) throughout the entire tissue thickness at several randomly selected locations within microislands were taken (n=3 locations per microisland). The percentage of viable cells was quantified by manual counting at two depths (33% and 75% height) per acquired stack using NIS Elements (Nikon).

Glass Acrylation and PDMS Mold Preparation.

In order to accurately track tissue development over time, microisland tissues were fabricated and immobilized on acrylated glass coverslips. Circular glass coverslips (21 mm, No. 1, Fisher Scientific) were cleaned using 30% hydrogen peroxide ($H_2O_2$) and 70% sulfuric acid ($H_2SO_4$), followed by thorough ethanol rinsing and air-drying prior to glass acrylation. Cleaned glass coverslips were incubated overnight using diluted acetic acid (9%), 3 (Trimethoxysilyl) propyl methacrylate, and 200-proof ethanol at 25° C. After incubation, the acrylated glass coverslips were rinsed in ethanol followed by air-drying.

Polydimethylsiloxane (PDMS) molds were prepared by combining SLYGARD 184 silicone elastomer curing agent and SLYGARD 184 elastomer base (Dow Corning Corporation). PDMS precursor solution was transferred onto a glass slide fixed with 200 µm thick spacers on all edges. A second slide was placed on top and the entire assembly was bound together by binder clips. The assembly was transferred into an oven at 70° C. for 2 h for curing of the PDMS. The cured PDMS was peeled off the assembly and three cylindrical holes with diameters of 6 mm were punched into the PDMS mold using a cork borer. The PDMS mold and acrylated glass coverslips were soaked in 70% ethanol under UV light for 24 h followed by complete air drying for at least 24 h to ensure complete sterilization. Before use in cell encapsulation, the PDMS mold with three cylindrical holes for tissue production was placed on the circular, acrylated glass coverslips and pressed down firmly to prevent leakage.

PEG-Fibrinogen Synthesis and Precursor Preparation.

PEG-fibrinogen was prepared as previously described. First, poly(ethylene glycol)-diacrylate (PEG-DA) was prepared by reacting linear PEG-OH (10 kDa) with acryloyl chloride and triethylamine. The product was precipitated in ice-cold diethyl ether, followed by vacuum drying for 48 h. Degree of acrylation was quantified by proton 1H NMR.

For PEG-fibrinogen synthesis, tris (2-carboxyethyl) phosphine hydrochloride (TCEP-HCl) was combined with 7 mg/ml fibrinogen in PBS with 8 M urea (1.5:1 TCEP to fibrinogen molar ratio). Next, for PEGylation of fibrinogen, PEG-DA was reacted with fibrinogen (4:1 molar ratio) for 3 h, precipitated in acetone and dissolved in PBS with 8 M urea. The reacted PEG-fibrinogen was dialyzed against PBS at 4° C. for 48 h followed by lyophilization. To characterize the PEGylated product, fibrinogen content was measured using Pierce BCA assay.

Lyophilized PEG-fibrinogen powder was re-dissolved in PBS to obtain a final fibrinogen concentration of 10 mg/ml. PEG-fibrinogen precursor solution was prepared by combining PEG-fibrinogen with 1.5% triethanolamine (TEOA), 3.96 µl/ml N vinyl pyrrolidone (NVP), and 10 mM eosin Y (Fisher Scientific) photoinitiator (in PBS).

HiPSC Dissociation and Microisland Formation.

HiPSCs were dissociated using Versene (clump hiPSC encapsulation) or Accutase (single hiPSC encapsulation, Innovative Cell Technologies) to form 3D engineered microislands (day −3). Clump or single hiPSCs were resuspended in mTeSR-1 media and centrifuged for 5 min at 200 g. The supernatant was aspirated using a glass Pasteur pipette and uniform aspiration was insured through inversion of the tube without disturbing the cell pellet. Clump or single hiPSCs were resuspended uniformly at a density of 55±8.5×10⁶ hiPSCs/ml of PEG-fibrinogen precursor solution using a wide orifice pipette tip. 10 µl of this mixture was added to each of the three cylindrical holes in the PDMS mold on acrylated glass coverslips and crosslinked using visible light (intensity of 48 mW/cm² at a distance 3 cm away) for 1 min. The PDMS mold surrounding the three crosslinked hydrogels (microislands) was then carefully detached and the acrylated glass coverslip with covalently coupled microislands was transferred to a 12 well plate (three microislands per well) and cultured in 2 ml mTeSR-1 media supplemented with 5 µM ROCK inhibitor for 24 h (day −3). On the two days following encapsulation (day −2, day −1), microislands were cultured in mTeSR-1 media with daily media exchange. On the third day post-encapsulation (day 0), cardiac differentiation was initiated. All encapsulations resulted into successfully, contracting cardiac tissues.

Differentiation of hiSPCs

2D Monolayer Differentiation of hiPSCs.

For 2D monolayer differentiation of hiPSCs, the composition of the media and timeline of differentiation was similar to that in a previously published protocol; 2D differentiating monolayers were used as controls. Briefly, hiPSCs were dissociated using Accutase, resuspended in mTeSR-1 media, counted, and centrifuged. HiPSCs were seeded at 1×10⁶ hiPSCs/well in a Matrigel coated 6-well plate with 4 ml mTeSR-1 media+5 µM ROCK inhibitor for 24 h (day −4). From day −3 until day 0, mTeSR-1 media was replaced daily. On day 0 of differentiation, media was changed to 4 ml RPMI/B27 without insulin+12 µM CHIR99021 (Selleckchem) for 24 h. Media was changed to 4 ml RPMI/B27 without insulin for an additional 48 h. On day 3, 2 ml RPMI/B27 without insulin and 5 μM IWP2 (Tocris) were combined with 2 ml old RPMI/B27 without insulin ("combined media") and cells were cultured until day 5, when media was changed back to RPMI/B27 without insulin. On day 7 and successively every three days, media was replaced with RPMI/B27.

3D Cardiac Differentiation of Clump and Single hiPSCs in PEG Fibrinogen Hydrogels.

Following the same protocol used for the 2D monolayer differentiation of hiPSC, on day 0 of differentiation, media was changed from mTeSR-1 to 2 nil RPMI/B27 without insulin+12 μM CHIR99021 media per well. After 24 h (day 1), media was changed to 2 ml RPMI/B27 without insulin. On day 3 of differentiation, media was replaced with 1 ml fresh RPMI/B27 without insulin, 5 μM IWP2, and 1 ml old RPMI/B27 without insulin and cultured for an additional 48 h. On day 5, media was switched back to 2 ml RPMI/B27 without insulin and followed by 2 ml RPMI/B27 media on day 7, media being replaced thereafter every three days. For subsequent characterization studies and comparisons to 2D sheets, clump encapsulated 3D tissues were used.

Parallel Plate Mechanical Compression Testing.

Acellular and cellular hydrogel microislands (diameter=3 mm) were tested for their compressive mechanical properties 24 h after tissue formation (day 2) using a micron-scale mechanical testing system (Microsquisher, CellScale). Force was calculated via cantilever beam deflection in response to user-defined displacement (17% displacement) with compression rate of 4 μm/s. All samples were tested in PBS at 34° C. The cantilever beam was composed of Tungsten (modulus=411 GPa) with a diameter of 304.8 μm. Stress-strain characteristics of acellular and cellular tissues were obtained and the elastic modulus was directly obtained within the 5% strain range.

Results.

Figure 8A:
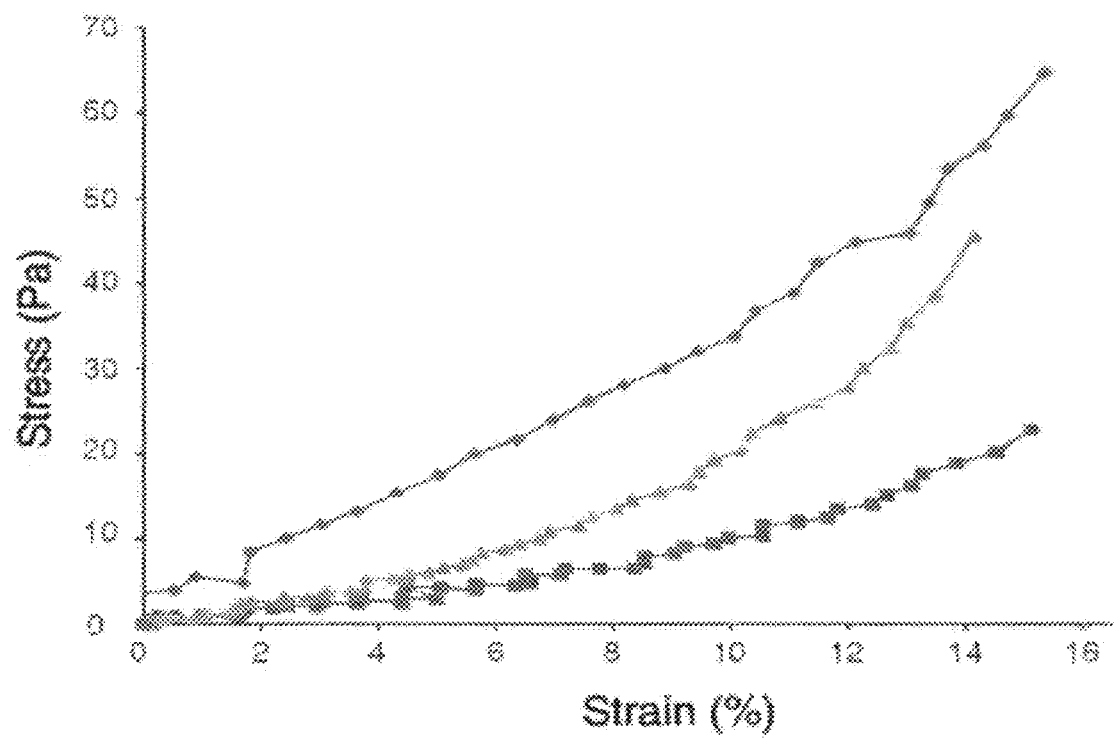
FIG. 8 (a-b) shows non-linear stress-strain behavior of cellular PEG-fibrinogen hydrogels 24 h post-encapsulation. (a) Stress-strain characteristics of clump encapsulated hiPSCs 24 h post-encapsulation show non-linearity. (b) The elastic modulus of acellular (507 Pa) and cellular (165±127 Pa) PEG-fibrinogen hydrogels was calculated based on the lower 5% of the stress-strain curves.
Figure 8B:
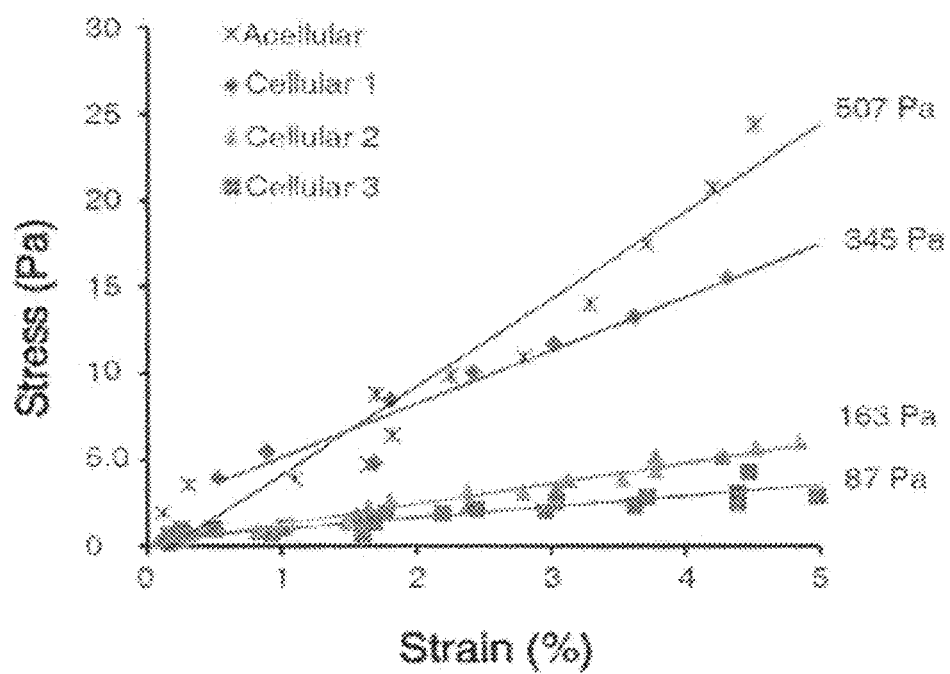

To form 3D tissues, clump or single dissociated hiPSCs were encapsulated in PEG fibrinogen hydrogels prior to the initiation of cardiac differentiation. HiPSCs are frequently cultured and passaged in clumps; this method has been found to result in higher cell viability and better maintenance of pluripotency. A drawback of this culturing method, however, is the inherent variability in clump size, which was considered to be a potential challenge when creating highly reproducible 3D cardiac tissues from hiPSCs. Therefore, the ability to create 3D tissues using both clump and single dissociated hiPSCs was established. To accomplish this, clump or single hiPSCs were combined with liquid PEG fibrinogen precursor solution and then photocrosslinked to create 3D tissues (FIG. 1a). To form 3D tissue "microislands," which was the geometry used for most experiments, crosslinking (1 min) was carried out in a removable PDMS mold with an acrylated glass base resulting in cylindrical tissues 6 mm wide and 200 μm thick (FIG. 1b, g). At 24 h post encapsulation (day 2), cellular microislands exhibited a tissue stiffness of 165±127 Pa (n=3); age-matched acellular microislands were stiffer (~507 Pa, FIG. 7); having previously been shown to support CM growth, PEG-fibrinogen can be remodeled and degraded by encapsulated cells over time. Both clump and single hiPSCs were uniformly distributed throughout the 3D microislands; microislands formed using single hiPSCs initially had a more homogeneous appearance due to lack of cell aggregates (FIG. 8a). Based on known challenges when handling hiPSCs in standard culture, viability of encapsulated cells was examined 24 h post-encapsulation (day –2); the majority of clump and single hiPSCs remained viable in their new, 3D microenvironment (FIG. 1c, h), similar to standard hiPSC passages (>50%), 3D microislands were cultured for three days followed by initiation of differentiation on day 0 (FIG. 1a). During the early stages of hiPSC culture within the tissue microislands, cells encapsulated following clump dissociation continued to grow as clusters, occupying the entire microisland volume quickly and forming a dense, multilayer cellular structure by day 14 (FIG. 1d-f). At the time of initiation of differentiation (day 0), more cell proliferation was observed on the tissue edge than at the center, forming a dense tissue ring around the perimeter of the microisland by day 5 (FIG. 8b). In comparison, for single encapsulated hiPSCs the time course of tissue formation was substantially longer;

encapsulated single cells first formed small colonies and then subsequently formed interconnected tissue structures (FIG. 1i-k). In both cases, cells continued to proliferate within the microislands following initiation of differentiation, as demonstrated by positive proliferating cell nuclear antigen (PCNA) staining on day 10 of differentiation, with the highest number of proliferating cells located on the tissue top and edges. Encapsulated cells first proliferated within the PEG fibrinogen hydrogel, filling the available volume, after which an increase in tissue thickness from ~200 μm to 300 μm was observed (between days 3 and 5). Cell outgrowth and tissue thickening continued to be observed over time (FIG. 8b).

Example 2: 3D Encapsulated hiPSCs Form Synchronously Contracting, Functional Cardiac Tissues One-step hiPSC encapsulation and cardiac differentiation process successfully resulted in synchronously contracting cardiac tissues with first areas of contraction by day 7 of differentiation for all performed hiPSC encapsulations. Microislands formed using both clump and single hiPSCs were all observed to contract (n>40 separate differentiations) with initiation of contraction occurring in localized areas between day 7 and day 11 depending on dissociation technique. Spontaneously contracting areas increased in number and synchronicity of contraction in both clump and single hiPSC encapsulated microislands over time, resulting in uniform contracting cardiac tissues by day 14.

Figure 9A:
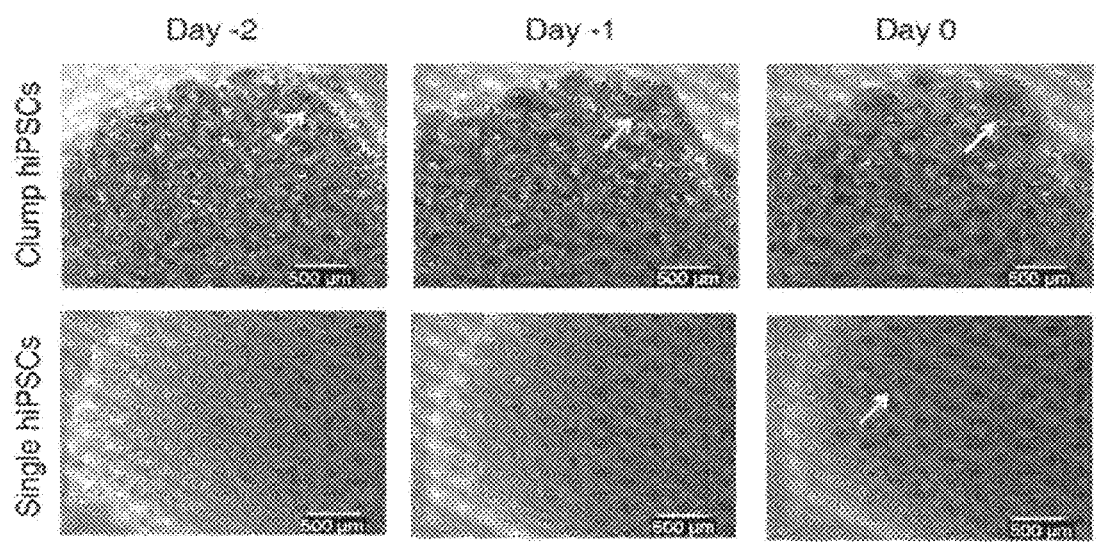
FIG. 9 (a-b) shows different pattern of cell proliferation and tissue development between clump and single encapsulated hiPSCs. (a) More proliferating hiPSCs using clump dissociation were observed on tissue edges, while encapsulated single hiPSCs proliferated independent of tissue location. (b) High magnification phase contrast images of day 5 and day 30 clump encapsulated hiPSCs show differences in tissue density and cell outgrowth onto acrylated glass. White arrows indicate locations with high number of proliferating cells.
Figure 9B:
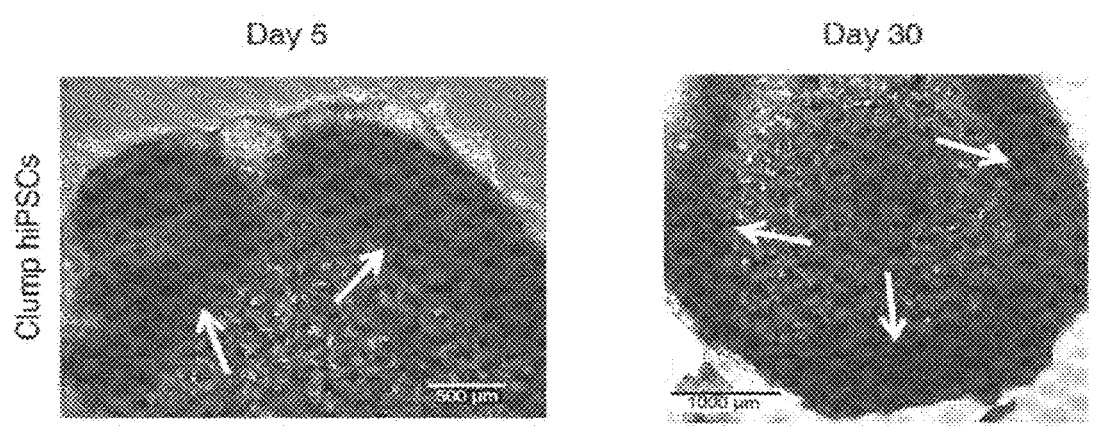

Video recordings of spontaneously contracting cardiac tissues were acquired on a phase contrast microscope (Ti Eclipse, Nikon) using a high speed camera (Andor Luca S) to determine frequency of contraction. Number of contractions per minute at early (day 8-day 15), intermediate (day 16-day 25), and late (day 26-day 50) time points were analyzed using NIS Elements and Image J (n=4 independent encapsulations). The frequency of contraction of these cardiac tissue microislands changed from 0.59±0.17 Hz (early differentiation, <day 16) to 1.53±0.25 Hz (late differentiation, day 25-36, FIG. 9) and remained at ~1.4 Hz during long-term culture (day 124). Microislands formed using clump hiPSCs showed first isolated and asynchronous areas of contraction along the edge of the tissues on day 7 of differentiation (compared to day 8 for control 2D cardiac monolayers). Microislands formed using single hiPSCs showed first spontaneously contracting areas on average two to four days later (day 9-11, n=3 separate differentiations) than microislands formed using clump hiPSCs (day 7, n>20). In contrast to the more rapid tissue development observed on the tissue edges in microislands formed using clump hiPSCs, is microislands formed using single hiPSCs did not display a consistent location for the first isolated areas of contraction within the tissue. Single hiPSC microislands also formed uniform contracting tissues, but frequency of contraction was slower, ~0.4 Hz (single) vs. 0.59±0.17 Hz (clump), during early stages of differentiation, and did not appear to be as strong compared to age-matched clump cardiac tissues. For all subsequent experiments, clump hiPSC encapsulations were chosen due to their higher batch to batch consistency, particularly with respect to the time point for initiation of contraction, as compared to single hiPSC encapsulations.

Example 3: Developing Cardiac Tissues Express Cardiac Genes and Cardiac Efficiency Similar to Control 2D Monolayers Tracking the ability to successfully and efficiently differentiate encapsulated hiPSCs into CMs, differentiation efficiency using flow cytometry and assessment of pluripotency and cardiac gene expression was shown to be similar to high efficiency 2D monolayer differentiation.

To determine the efficiency of cardiac differentiation in 3D, the expression of cTnT was evaluated by flow cytometry on day 20 microislands. On day 20, 2D sheets were washed with PBS and incubated in 0.25% trypsin (EDTA, Mediatech) at 37° C. for 5 min. Age-matched 3D tissues were washed with PBS followed by 2 h incubation at 37° C. on a rotator (Boekel Orbitron Rotator, Model 260250, Boekel Scientific) with collagenase Type 2 (1 mg/ml, Worthington) in 120 mM NaCl, 5.4 mM KCl, 5 mM MgSO4, 5 mM Na-pyruvate, 20 mM glucose, 20 mM taurine, and 10 mM HEPES (pH 6.9) supplemented with 30 µM CaCl2, followed by incubation in 0.25% trypsin (EDTA) at 37° C. for 5 min. All cells (in 2D sheets and 3D tissues) were then singularized by pipetting (using a 1000 µl pipette), transferred to a centrifuge tube with RPMI20 media (RPMI 1640 media with 20% PBS) and centrifuged for 5 min at 200 g. The supernatant was removed and the cell pellet was resuspended in 4% paraformaldehyde and incubated for 20 min at 25° C. Cells were centrifuged for 5 min at 200 g, supernatant was aspirated and the cell pellet was resuspended in 90% cold methanol and incubated at 4° C. for 15 min. The fixed cells were blocked with 5% BSA in PBS for 5 min and centrifuged for 5 min at 200 g. After washing two more times with 5% BSA in PBS, cells were incubated in 100 µl primary antibody diluted in 0.5% BSA and 0.1% Triton X-100 in PBS. The primary antibody combination cTnT/Ki67 was chosen. Antibodies used are provided in Table 1.

TABLE 1

Primary and secondary antibodies for immunofluorescence and flow cytometry.

| Antibody | Specification | Dilution |
| --- | --- | --- |
| Sarcomeric alpha actinin | Mouse IgG1/Sigma-Aldrich/A7811 | 1:200 (IF) |
| Connexin 43 | Rabbit IgG/Sigma-Aldrich/C6219 | 1:200 (IF) |
| Proliferating cell nuclear antigen | Mouse IgG2a/Millipore/MAB1691 | 1:200 (IF) |
| Cardiac troponin T | Mouse IgG1/Thermo Scientific/MA512960 | 1:200 (IF), 1:20 (FC) |
| Ki67 | Rabbit IgG/Abcam/ab92742 | 1:200 (IF), 1:100 (FC) |
| Mouse isotype control | Mouse IgG1/Thermo Scientific/MA110406 | 1:100 (FC) |
| Rabbit isotype control | Rabbit IgG/Thermo Scientific/PA523090 | 1:50 (FC) |

TABLE 1-continued

Primary and secondary antibodies for immunofluorescence and flow cytometry.

| Antibody | Specification | Dilution |
| --- | --- | --- |
| Secondary antibody | Alexa 488 Goat anti-Rabbit IgG/A-11008 | 1:200 (IF), 1:1000 (FC) |
| Secondary antibody | Alexa 568 Goat anti-Mouse IgG/A-11004 | 1:200 (IF) |
| Secondary antibody | Alexa 647 Goat anti-Mouse IgG/A-20990 | 1:1000 (FC) |

Figure 2C:
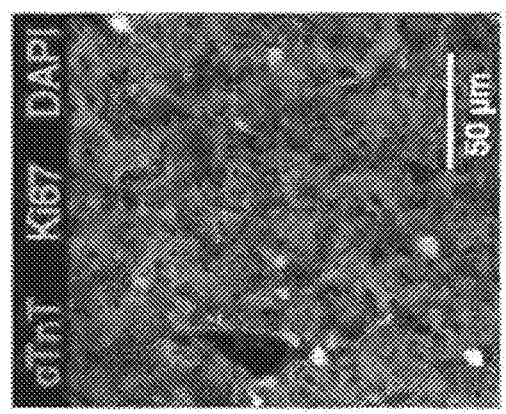
FIG. 2 (a-d) shows 3D developing cardiac tissues enabling efficient cardiac differentiation similar to control 2D monolayers and develop well-defined sarcomeres over time. (a) Representative flow cytometry results from day 20 cardiac tissues and (b) comparison of analysis from 3 biological replicates of day 20 cardiac tissue (3D) and aged-matched 2D monolayers showed comparable differentiation efficiency. (c) Cardiac marker cTnT and proliferation marker Ki67 were also observed using immunofluorescence staining of day 20 cardiac tissues. n=3 biological replicates per group. P<0.05, **vs. 2D, (d) Sarcomere definition and alignment becomes more pronounced with culture time. Immunofluorescence staining with cardiac marker αSA on days 10, 20, and 30 of differentiation show better defined and aligned sarcomeres over time.
Figure 2B:
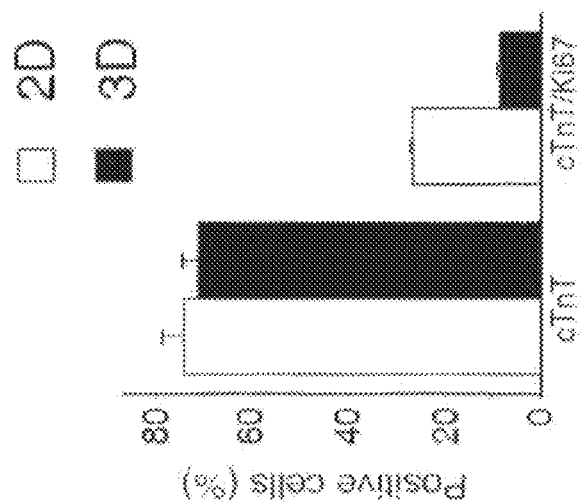
Figure 2A:
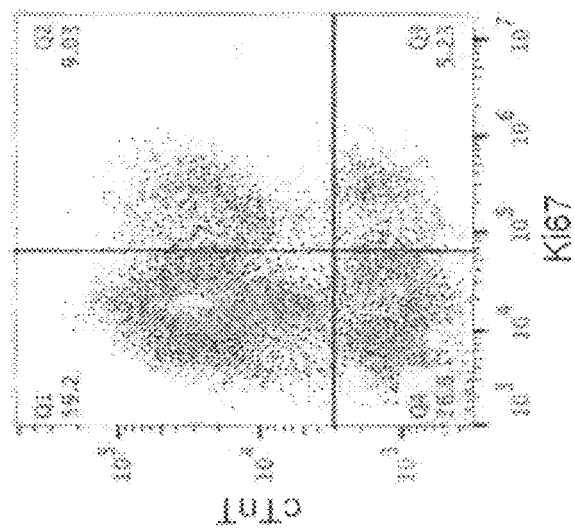

After incubation at 4° C. overnight, cells were washed with 0.5% BSA and 0.1% Triton X-100 in PBS, which was repeated twice. Cells were further incubated in 100 µl secondary antibody diluted in 0.5% BSA and 0.1% Triton X 100 in PBS for 30 min at room temperature, protected from light. Finally, cells were washed with 0.5% BSA and 0.1% Triton X-100 in PBS three times and resuspended for analysis in 500 µl 5% BSA in PBS. Samples were run on a BD Accuri C6 (BD Biosciences) and were analyzed using FlowJo V10. The results showed 71.4±3.2% cTnT positive cells; the proliferation marker Ki67 was also evaluated, with 8.4±0.7% Ki67 positive cells (FIG. 2a); these results were similar to age matched 2D cardiac monolayers with 74.3±4.4% cTnT and 26.6±0.5% Ki67 positive cells (FIG. 2b); stained tissue samples also confirmed the expression of cTnT and Ki67 (FIG. 2c).

Figure 2D:
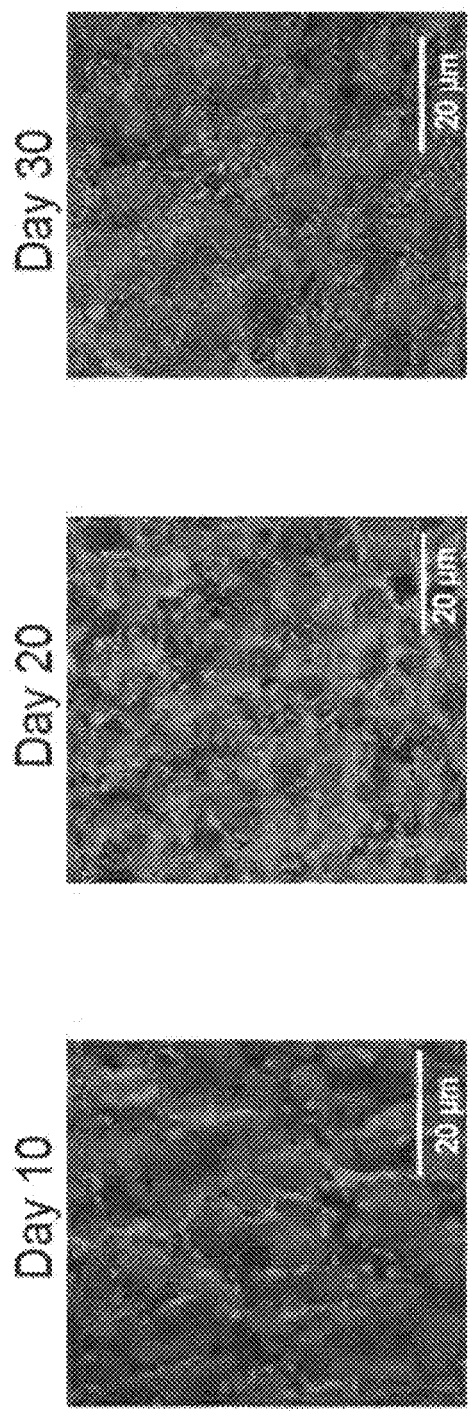

To assess protein expression of cardiac marker sarcomeric α-actinin (αSA) and gap junction protein connexin 43 (Cx43) of 3D developing cardiac tissues, samples were prepared for immunofluorescence. First, cardiac tissues were fixed using 4% paraformaldehyde (Electron Microscopy Sciences) or 50/50 ice cold acetone/ethanol (for Cx43 staining). Fixed tissues were permeabilized with PBS-T (PBS with 1% bovine serum albumin (BSA) and 0.2% Triton X 100) and blocked (3% fetal bovine serum (FBS, Atlanta Biologicals) in PBS). Samples were consecutively incubated in primary and secondary antibody (Table A). All primary and secondary antibodies were applied for at least 24 hours at 4° C. Cell nuclei were stained with 4',6-diamidino-2-phenylindole (DAPI, Molecular Probes). All fluorescently labeled samples were visualized using a Nikon Alsi confocal microscope. Immunofluorescence staining for αSA on days 10, 20, and 30 cardiac tissues revealed sarcomere development over time with better defined and aligned sarcomeres by day 30 of differentiation (FIG. 2d).

Figures 3D, 3E:
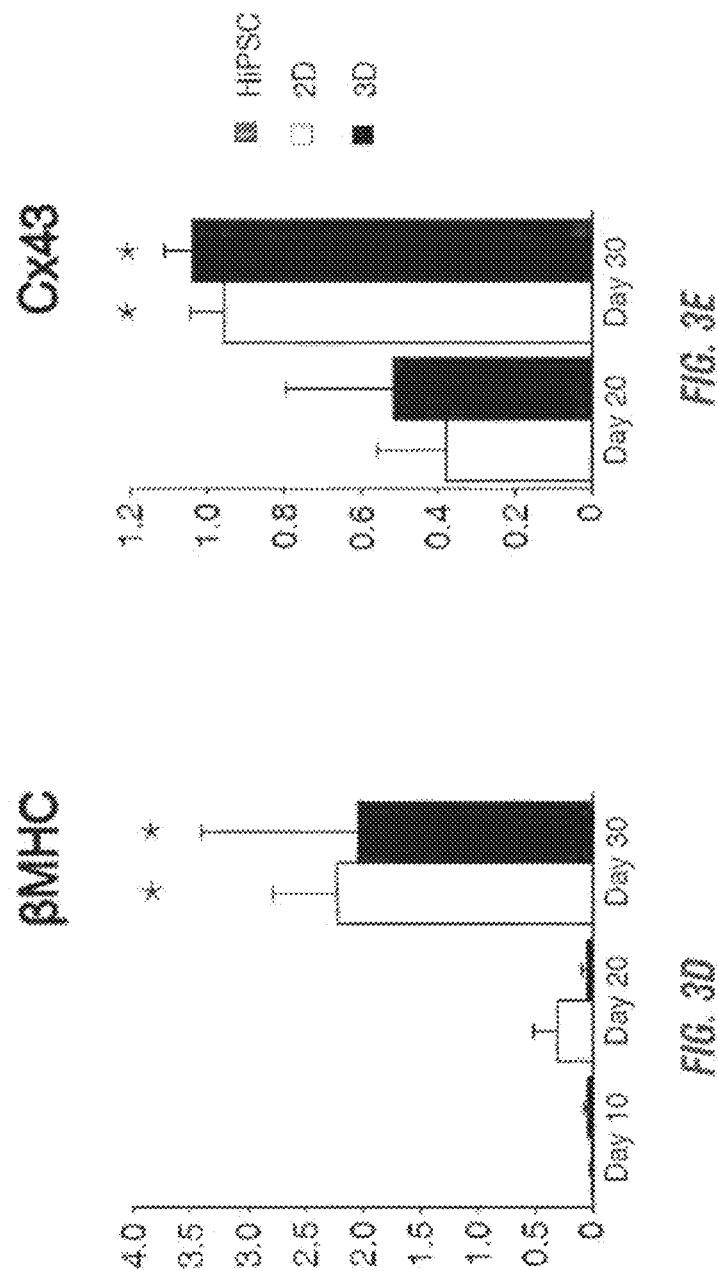
FIG. 3 (a-e) shows cardiac gene expression in cardiac tissues similar to control 2D monolayers. (a) Pluripotency gene Oct4 decreases significantly over time while cardiac genes (b) MLC2v, (c) αMHC, (d) βMHC, as well as (e) the functional gene Cx43 show trends towards CM maturation. All mRNA levels were normalized to the housekeeping gene GAPDH. n=3 biological replicates per group. P<0.05, # vs hiPSCs and day 0; * vs. earlier time point.

Results assessed by flow cytometry showed that pluripotent gene expression decreased while cardiac and functional gene expression increased along the time course of 2D and 3D differentiation. Changes in gene expression were assessed over time for 3D microislands and age-matched 2D controls. In order to assess maintenance of pluripotency and the time course of cardiac development following encapsulation in PEG-fibrinogen, gene expression was quantified using qRT-PCR. Total RNA was extracted from hiPSCs, 2D monolayers, and 3D tissues on days 0, 10, 20, and 30 of differentiation (n=3 independent differentiations) using Nucleospin RNA kit (Macherey-Nagel). Quantitative real time PCR (qRT-PCR) was performed using SuperScript III Platinum One-Step qRT-PCR kit (Invitrogen) in conjunction with Taqman probes (Integrated DNA Technologies). Equal amounts of RNA (50 ng/19 µl) were used for each measurement. The qRT PCR protocol consisted of 1 cycle at 50° C. (15 min), 1 cycle of 95° C. (3 min), 45 cycles of 95° C. (15 s) and 55° C. (30 s). Gene expression levels were normalized to the housekeeping gene GAPDH using the 2-ΔCt method. Duplex qRT PCR was used for Oct4, MYL2, and Cx43 genes; MYH6, MYH7, and GAPDH were quantified separately. Three days post-encapsulation (day 0), Oct4 gene expression in 3D microislands or 2D monolayers continued to be similar to hiPSCs (day 3). By day 10 of differentiation, Oct4 expression had decreased significantly compared to hiPSCs and remained low after that (FIG. 3a). MLC2v, an early cardiac marker, increased in both 2D monolayers and 3D tissues from day 20 to day 30 of differentiation (FIG. 3b). The αMHC gene has been shown to have a higher expression early during heart development, with subsequent downregulation, along with an upregulation of βMHC; this trend was observed in microislands between days 10 and 30 (FIG. 3c, d). The significant increase in βMHC gene expression by day 30 of differentiation suggests cardiac maturation over time, similar to 2D monolayer differentiation. Day 30 3D tissues and control 2D monolayers showed significant increase in Cx43 gene expression, suggesting the maturation of cell-cell junctions between adjacent CMs (FIG. 3e).

3D Cardiac Tissues Exhibit Similar Calcium Handling than 2D Cardiac Sheets

To immobilize cells for proper calcium transient acquisition, glass coverslips (21 mm, No. 1, Fisher Scientific) were coated with PDMS using a WS-400-6NPP spin coater (Laurell Technologies Corporation). Briefly, SLYGARD 184 silicone elastomer curing agent was mixed with SLYGARD 184 elastomer base (Dow Corning Corporation) at a ratio of 1:10, applied on the glass coverslips and evenly spin coated to obtain PDMS coated coverslips. These were dried at 60° C. for several hours, sterilized using 70% ethanol, and further dried under sterile conditions for at least 24 h. In order for successful single CM attachment, 1× fibronectin in ice cold ultrapure water was applied on PDMS coated coverslips and incubated for at least one hour at room temperature.

Day 14 2D monolayers and 3D tissues were dissociated using 0.25% trypsin (EDTA) at 37° C. for 5 and 8 min, respectively. Cells were singularized by pipetting, added to RPMI20 media49, and centrifuged for 5 min at 200 g. Singularized cells were resuspended in RPMI20+5 μM ROCK inhibitor and transferred onto fibronectin coated PDMS glass coverslips. Cells were incubated for 48 h to ensure uniform cell attachment. Media was then switched to RPMI/B27 and cells maintained for 3 to 5 days. CM calcium transient recordings were obtained using an IonOptix Myocyte Calcium and Contractility Recording System. Samples were incubated in 5 μM Fura-2AM dye (Molecular Probes) in 37° C. warm Tyrode's solution (1.8 mM CaCl2, 5 mM glucose, 5 mM HEPES, 1 mM MgCl2, 5.4 mM KCl, 135 mM NaCl, and 0.33 mM NaH2PO4, pH 7.4) for 30 min. CMs were paced at frequencies from 0.5 to 2.0 Hz (0.5 Hz increments) and stimulated at 30 V. Calcium transient duration at 50% and 80% time to baseline was recorded. In addition to responses to outside electrical stimuli, response to 0.5 μM isoproterenol was studied on un-paced CMs.

Functional properties of differentiating CMs are critical for their contractile function and calcium handling. The contractile function and calcium handling properties are critical functional features of differentiating CMs. To study the electrophysiological properties of 3D cultured CMs, day 14 cardiac tissues and aged-matched 2D sheets were dissociated to determine differences in calcium handling. CMs were paced from 0.5-1.5 Hz (0.5 Hz increments) with 1:1 correspondence to outside pacing frequencies. Time to baseline 50% and 80% of calcium transients of 3D cultured CMs were similar to control 2D monolayer cells (FIG. 4a, b). Slightly longer time to baseline could be attributed to a more extensive dissociation process to singularize 3D cultured CMs (FIG. 4c). The increase in pacing frequency was accompanied by a significant shortening in calcium transient duration, this is a physiologic response recognized in human healthy myocardium. As expected, isoproterenol, a β adrenergic agonist, increased the spontaneous beating rate from 33 beats per min (pre-isoproterenol) to 60 beats per min (post isoproterenol) as well as significantly shortened time to baseline 50% and 80% (FIG. 4d, e).

One-Step 3D Cardiac Tissues Develop Mature Structural Features Over Time

In addition to similar gene expression, protein expression, and electrophysiological similarities to age-matched 2D monolayers, 3D tissue formation showed advantages during long-term culture which revealed development in their ultrastructural features.

Figure 10A:
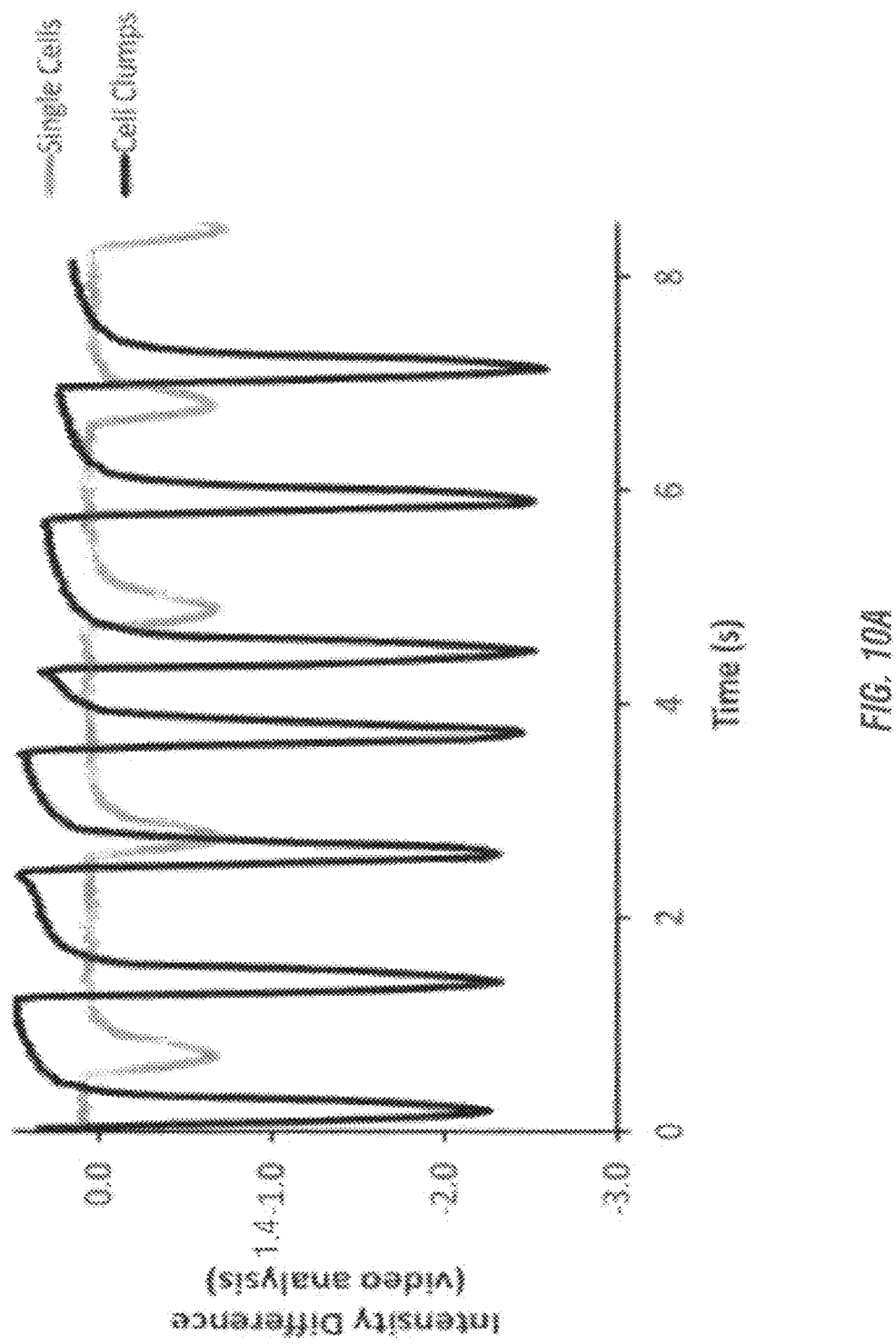
FIG. 10 (a-b) shows contraction properties of 3D cardiac tissues. Frequency of contraction increased in cardiac tissues over time. (a) Stronger contracting tissues of clump encapsulated hiPSCs (vs. single encapsulated hiPSCs) were accompanied by (b) an increase in contraction frequency, ranging from 0.66±0.18 Hz (Early) to 0.99±0.29 Hz (Intermediate) to 1.37±0.04 Hz (Late), n=3.
Figure 10B:
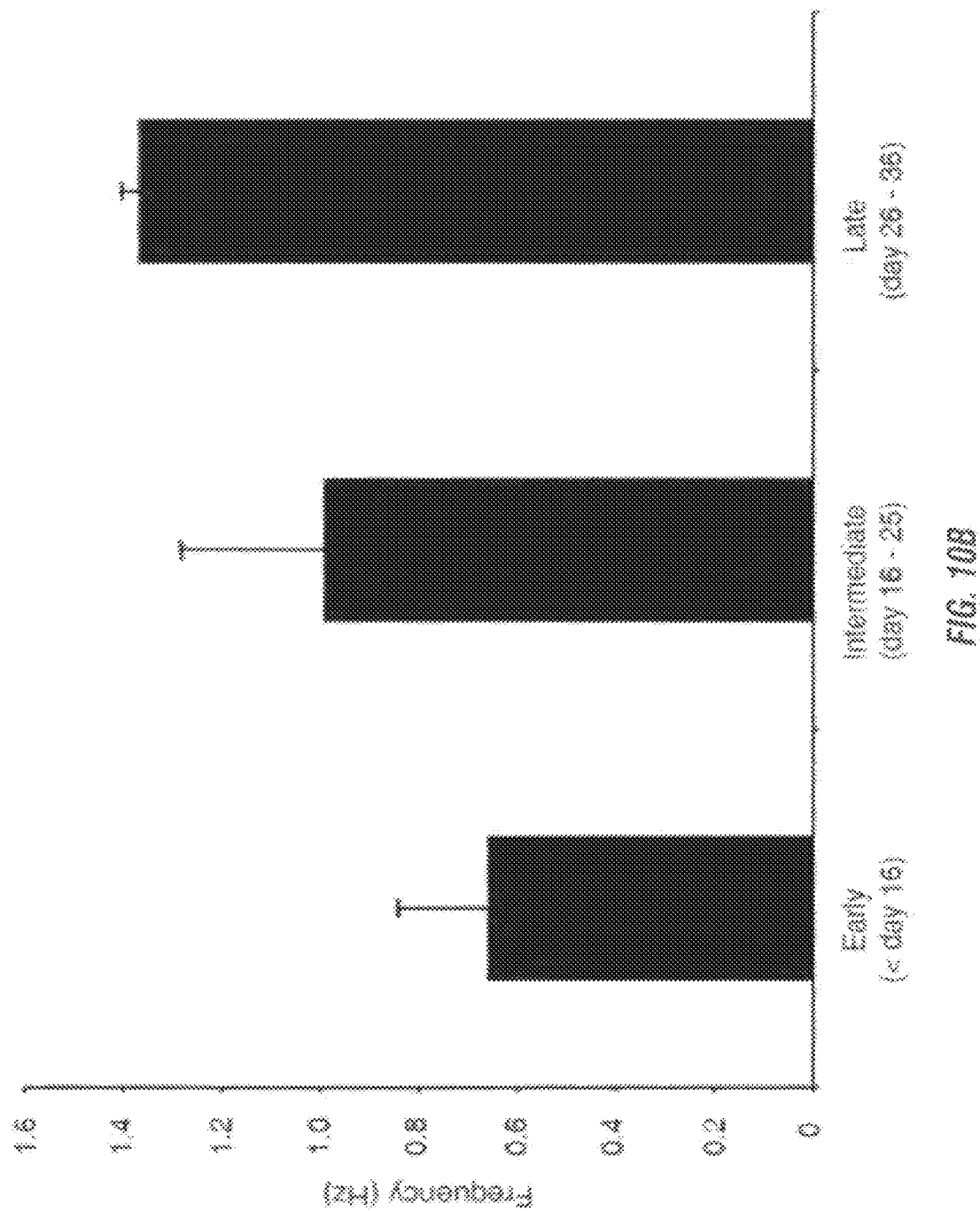

Supplemental to staining for the cardiac marker αSA, TEM images of day 24 cardiac tissues show the presence of Z-discs and mitochondria (FIG. 10), which suggest the progression towards functional CMs. Day 24 and day 124 old spontaneously contracting cardiac tissues were fixed in 3% glutaraldehyde (Electron Microscopy Science) at 4° C. before shipping to the pathology core at Icahn School of Medicine at Mount Sinai, N.Y. Tissue samples were sectioned (50-60 nm) and stained with Uranyl Acetate Solution and Reynold's Lead Citrate Solution. Processed tissue slices were examined using a transmission electron microscope (H-7650, Hitachi High Technologies). 3D cultured CMs continued to mature post day 30, leading to the display of ultrastructural features that have not been reported in any other in vitro human SC-CM study yet.

Usually, to achieve more mature, aligned, and uniform contracting cardiac tissues, pre-differentiated SC-CMs had to be dissociated and re-assembled with a biomaterial to form 3D tissues, followed by culture methods including outside stimuli like mechanical stretching or electrical pacing. However, encapsulated hiPSCs that were cultured and differentiated directly in PEG-fibrinogen hydrogels self-aligned, in particular on tissue edges, by day 30 of differentiation (FIG. 2d).

Figure 5A:
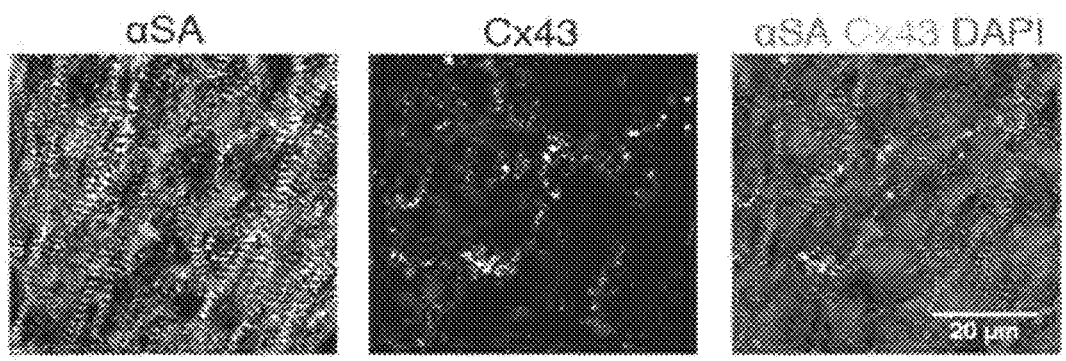
FIG. 5 (a-b) shows 3D cultured CMs displaying aligned sarcomeres and mature ultrastructural features. (a) In addition to defined sarcomeres, CMs express Cx43 on their terminal ends. (b) CMs with highly aligned sarcomeres and large, elongated cell nuclei are produced within PEG-fibrinogen hydrogels.
Figure 5B:
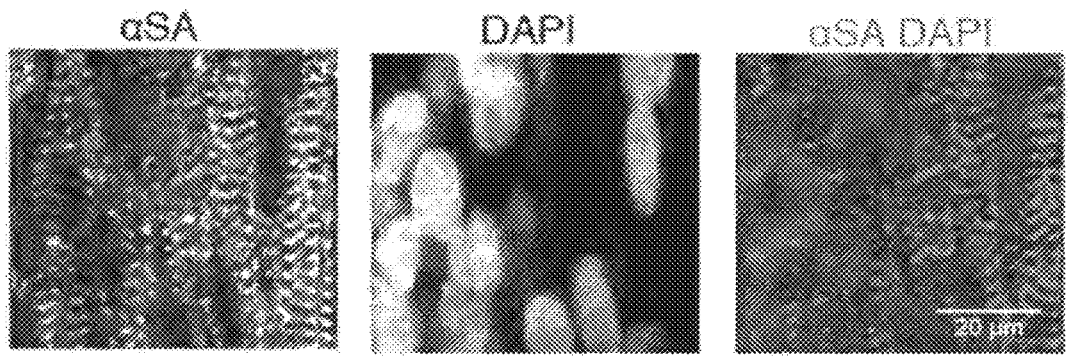
Figures 11A, 11B, 11C:
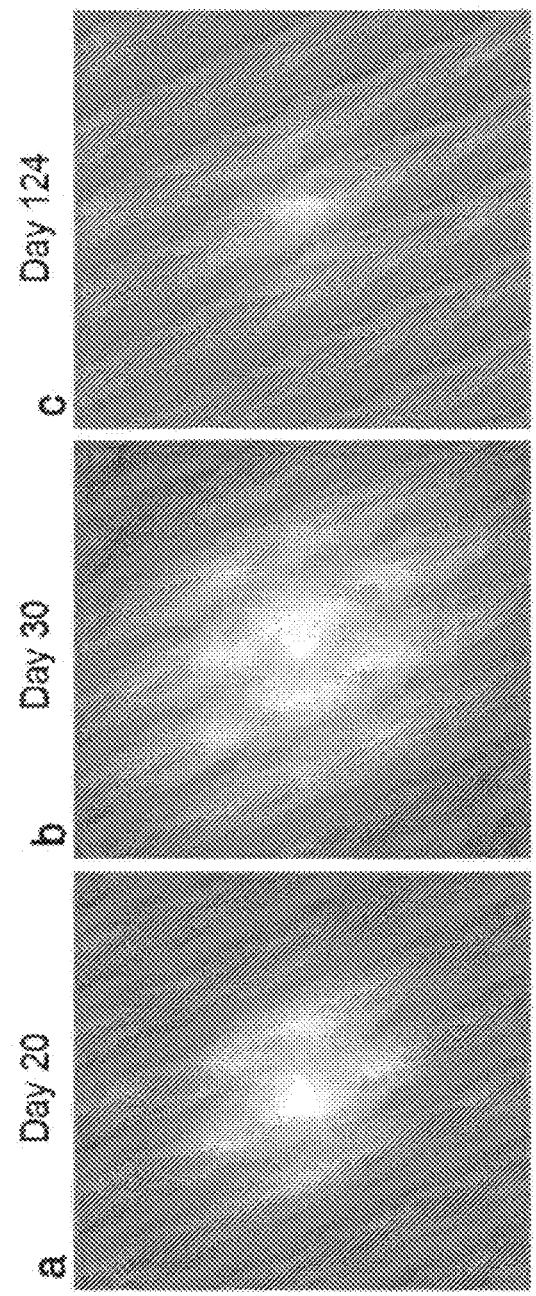
FIG. 11 (a-d) shows sarcomere of selected αSA-stained cells with more alignment of time transitioning from no visible rings (day 20) to visible, full rings (day 30) to more defined, aligned (direction of sarcomeres) rings (day 124). (d) Sarcomere distance on day 124 was quantified by generated intensity plots (increased gray scale represents existing sarcomere).
Figure 11O:
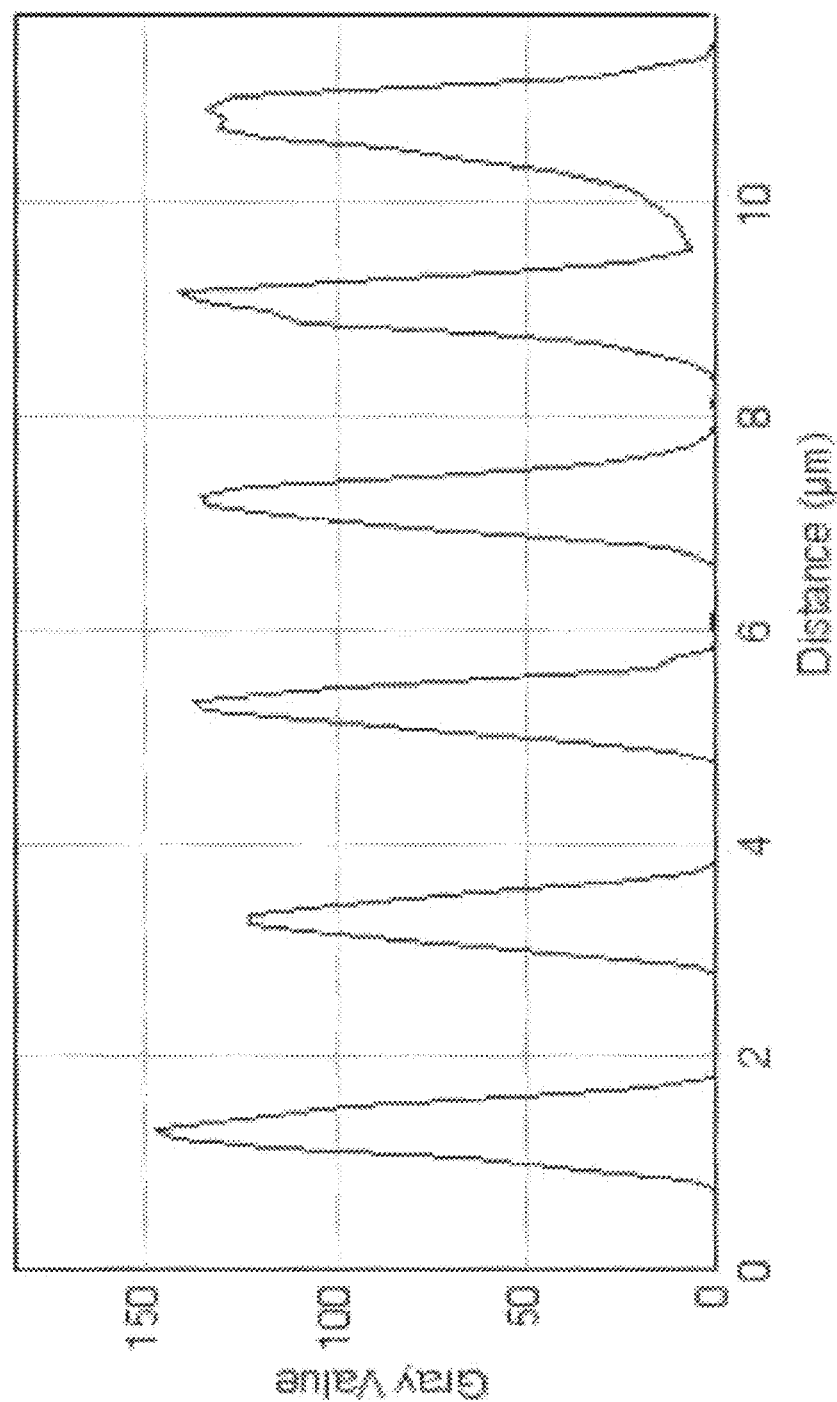

Throughout the differentiation process, sarcomere alignment of days 14, 30, and 124 αSA stained cardiac tissues was analyzed using Image J software version 1.48q (NIH) in affiliation with the fast Fourier transform (FFT) analysis tool. Images were imported into Image J; sarcomere alignment was determined by manually drawn linear paths along visible sarcomeres. In addition to sarcomere alignment, day 124 αSA stained CMs were used to quantify sarcomere length. Likewise, manually drawn linear paths along well defined sarcomeres (n=10 CMs) were used to collect an intensity profile for each chosen CM where distance between peaks was analyzed using Excel. Sarcomeres for FFT were selected based on continuity of sarcomeres in a single field of view. Using fast Fourier Transform (FFT), analysis of immunofluorescence images from days 20, 30, and 124 cardiac tissues showed better defined sarcomeres over time (FIG. 11a-c). Although some discrete sarcomere structure was observed during early stages of differentiation (day 20), progression towards a mature phenotype was observed on day 124 with 1.9±0.1 sarcomere spacing (FIG. 11d), similar to mature CMs Long-term cultured cardiac tissues (day 124) showed highly aligned CMs and subsequently, highly aligned, organized, and well-defined sarcomeres with large and elongated cell nuclei (FIG. 5a). Additionally, CMs showed gap junctions on the terminal ends (FIG. 5b). The cells' ultrastructure and internal features on day 124, visualized by TEM, show numerous mitochondria, well-defined Z-bands, H-bands, intercalated discs on the polar ends, gap junctions on the longitudinal side (FIG. 5c), basement membrane with caveolae, as well as T tubules aligned with Z-bands (FIG. 5d), which has only been detected in isolated CMs.

Figure 6A:
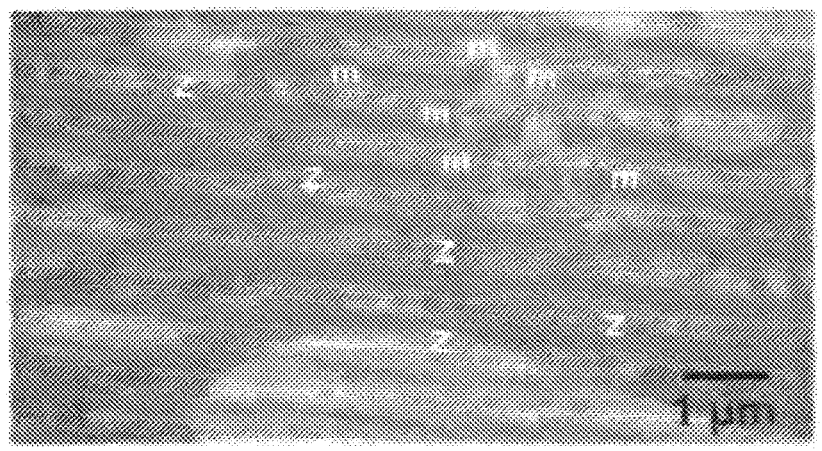
FIG. 6 (a-c) shows 3D microislands develop into cardiac tissues with CMs that display mature ultrastructural features. (a) Day 24 cardiac tissues show first ultrastructural features of a muscle cell including mitochondria (m) and Z-bands (Z). (b) Ultrastructural features of 124 day old 3D cardiac tissue shows sarcomere structures, including Z-bands (Z), H-zones (H), intercalated discs (ID), gap junctions (GJ), as well as mitochondria (m). (c) Additionally, basement membrane (bm) with caveolae (C), mitochondria with well-defined cristae, and T-tubules (T) adjacent to Z bands, a key component of functional CMs.
Figure 6B:
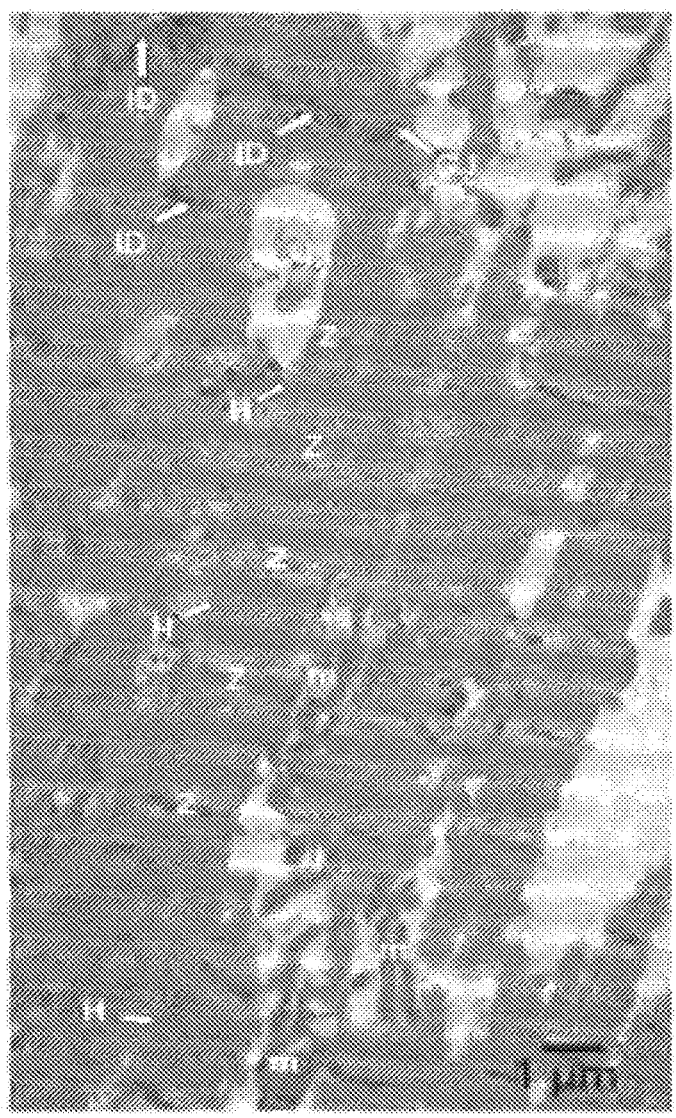
Figure 6C:
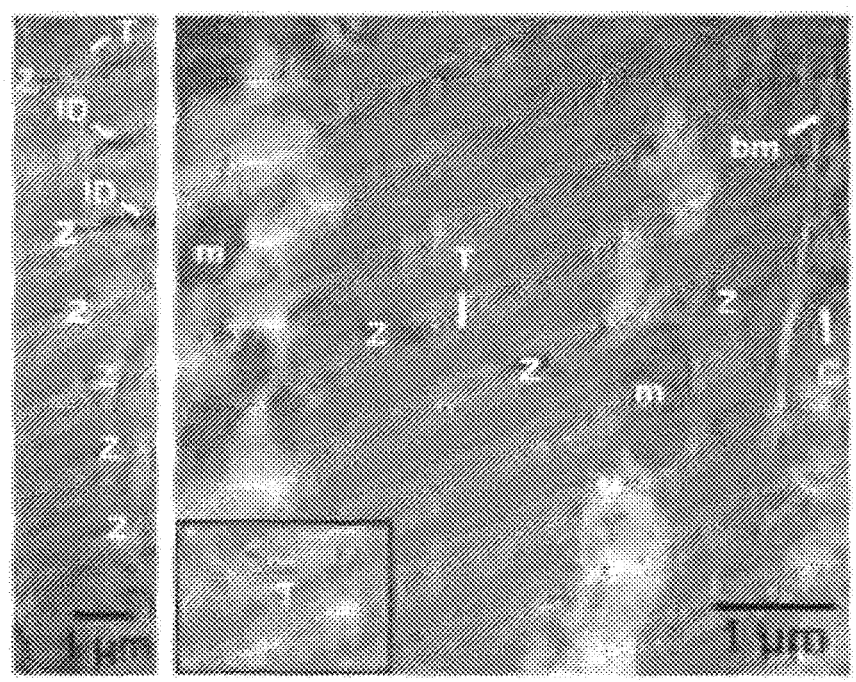

Multiple 3D Geometries Support Cardiac Tissue Formation Through Differentiation in PEG Fibrinogen Leveraging knowledge gained utilizing immobilized microislands to directly create functional cardiac tissues through 3D differentiation of hiPSCs in PEG-fibrinogen hydrogels, this one-step approach was then successfully extended to a range of geometries. Tested geometries using clump encapsulated hiPSCs included, but were not limited to, microislands (FIG. 6a), cardiac discs, strings, macrotissues, and microspheres. Cardiac discs, which have a similar tissue shape than microislands, were cultured in suspension with larger tissue diameter (>8 mm compared to 6 mm for microislands). Similar to microislands, cardiac discs also showed variations in cell proliferation over time but also resulted in uniform contracting tissues by day 14. A cardiac string with tissue diameter of 642±230 µm (n=3 locations) was produced, where cell proliferation was more uniform (no locational differences. Another tested tissue geometry included macrotissues (FIG. 6b), with >2 mm tissue diameter and 800-900 µm tissue thickness. First contracting areas were visible on day 7 of differentiation, resulting in very strong, uniform contractions early during differentiation (day 12), which remained strong over the entire culture period. Additionally, microspheres (FIG. 6c) with 280±70 µm (n=25) in diameter were cultured that resulted in uniform contracting spheres. Finally, all cardiac tissues were successfully dissociated into single CMs (FIG. 6d).

Differentiation of encapsulated hiPSCs to directly produce cardiac tissues in vitro opens a wide range of possibilities in the field of cardiac tissue engineering. The above results demonstrate that hiPSCs can be readily and efficiently encapsulated and differentiated in PEG-fibrinogen hydrogels to produce synchronously contracting cardiac tissues with similar gene expression and calcium handling than age-matched 2D cardiac monolayers. This method has advantages over 2D monolayer differentiation in that it enables long-term CM culture and maturation without having to disrupt the CMs post-differentiation and requiring re-formation of inherent cell-cell junctions, which is notoriously problematic for CMs, particularly as they mature. The minimal cell handling requirements and applicability of this cardiac tissue production technique to a wide range of tissue sizes and shapes facilitates high throughput, cost-effective, 3D human cardiac tissue availability for a range of future applications. PEG-fibrinogen can be rapidly photo-crosslinked using a nontoxic photoinitiator and visible light to form hydrogels. The hiPSC encapsulation procedure in soft (<500 Pa) PEG-fibrinogen hydrogels established in this study allows for hiPSC survival with maintenance of pluripotency for at least three days. Extended PEG-fibrinogen encapsulated hiPSC culture periods have not been investigated; however, other biomaterials have previously been used for large-scale hPSC culture and expansion. The chosen cell seeding density has been proven successful in forming continuous tissues; results showed that even with a 50% decrease of initial hiPSC seeding density, cell proliferation and cardiac contraction was initiated in 3D PEG-fibrinogen hydrogels (FIG. 12A-H); this robustness is not applicable to production of contracting 2D monolayers, where having a tightly defined initial cell seeding density is critical to success. Initial hydrogel stiffness is believed to play an essential role in successful 3D culture, proliferation, and cardiac differentiation, while initial cell seeding density may influence the uniformity of contraction within the cardiac tissue over time. Both of these factors directly influence the degradation rate and remodeling of PEG-fibrinogen hydrogels over time, allowing cells to secrete ECM proteins and form a continuous tissue.

During initial stages of stem cell differentiation, a steady increase in frequency of spontaneous contraction over time (day 10-day 36) is observed, which might be due to the development of stronger cell-cell junctions and better calcium handling between developing SC-CMs. The steady increase in contraction frequency diminished around day 30-40, after which spontaneous contractions remained constant at ~1.4 Hz. These findings have to be taken into account when modeling the human heart; human heart rate in vivo slows down significantly during maturation (~3.0 Hz during fetal stage to 1.0-1.5 Hz in adults).

CM proliferation is a phenomenon seen during fetal heart growth and early post-natal stages, after which diminishes over time. On day 20 of cardiac differentiation, higher percentages of proliferating CMs were detected in 2D monolayers as compared to 3D cardiac tissues, while both containing a similar percentage of cTnT positive cells. Other cellular properties, including cardiac gene expression and calcium handling, were similar between 2D and 3D at this time point. Therefore, we believe that 3D culture conditions and a more physiological microenvironment might be the cause for lower degrees of CM proliferation and not due to CM maturation.

During early stages of differentiation (day 14), SC-CMs exhibit mechanical and electrical features that are not well developed. Although 2D and 3D cultured SC-CMs respond to outside pacing frequencies up to 1.5 Hz, higher maximum capture rates at later time-points are desired. Increased beating rates of spontaneously contracting 3D cultured CMs in response to isoproterenol suggests that β-adrenergic signaling is operational in early stage CMs.

Human adult CMs are difficult to obtain for experimentation and are desired for myocardial repair in the adult patient for better mechanical and electrical integration, the process of human CM maturation is not studied yet but will provide important insights about adolescence and how the human heart remodels after birth, as well as provide more physiologically relevant features for toxicology screening and disease modeling of the adult human myocardium. Here, 3D differentiated and cultured SC-CMs present sarcomere spacing of 1.9±0.1 µm, similar to mature CMs. Furthermore, ultrastructural features of mature CMs were identified on day 124 of culture; future analysis at additional time points will help to identify when these ultrastructural features first appeared. Although morphological and functional SC-CM maturation has been observed in vitro, no T tubule formation has ever been detected in SC CMs. T-tubule formation and other mature ultrastructural features that are important in contraction excitation coupling have been detected in our long-term cultured CMs; the appearance of these features might be due to the continuous 3D microenvironment that allowed cells to secrete their own ECM proteins.

The successful formation and long-term maintenance of engineered cardiac tissues in the immobilized microisland/cylindrical disc morphology employed by this study was surprising, given that formation of engineered cardiac tissues with cardiomyocytes has typically required mechanical or electrical stimulation and more aligned geometries. As expected, this geometry did have some drawbacks; this study showed that the microisland/disc morphology (both when immobilized on acrylated glass and in suspension culture) results in tissues that are not uniform across the entire microisland, at least at the 6 mm diameter tested. Since the differences where observed prior to the onset of contraction, this phenomenon might be explained due to space limitations that the microisland centers; in comparison, hiPSCs on microisland edges have the ability to grow outwards from the original hydrogel boundaries. In a previous study, a similar tissue morphology (scaffold-free tissue patch) showed higher levels of cardiac maturation and CM purity on tissue edges compared to tissue centers. Furthermore, their tissue centers also contained non cardiac cells with fragmented cell nuclei. Additional testing will be required to determine the whether observed locational differences in microisland cardiac tissues formed in this study are also observed at smaller diameters or when using alternative fabrication techniques, such as microprinting, versus molds.

Although creation of microislands has advantages for in vitro assays, many applications have differing optimal cardiac tissue geometries. In addition using a suspension culture approach maximizes surface area for nutrient diffusion into the tissue. Therefore, translation of the one-step approach established in this study to additional tissue sizes and shapes was investigated. Tested geometries included, but were not limited to, printable microislands, for potential high throughput drug-screening applications, macrotissues, for large-scale mechanical testing, and microspheres for large-scale production of injectable cardiac tissue spheroids. Finally, if desired, all cardiac tissues can be dissociated into single CMs for in-depth single-cell analysis, such as automated patch-clamping (FIG. 5b). Compendiously, this robust one-step hiPSC encapsulation technique for producing synchronously contracting and functional cardiac tissue will ease and improve the cardiac tissue formation process.

The above specification provides a description of various methods of generating three-dimensional cell cultures or tissues, compositions of the same, methods of use, treatment and diagnosing. Since many embodiments can be made without departing from the spirit and scope of the invention, the invention resides in the claims.

What is claimed is:

1. A method of producing a three-dimensional cardiac tissue comprising:
   combining a population of pluripotent stem cells (PSCs) with a hydrogel precursor solution to form a PSC suspension, the hydrogel precursor solution comprising an acrylate component and a natural hydrogel-forming component comprising one or more of fibrinogen, collagen, gelatin, hyaluronic acid, elastin, fibronectin, laminin, fibrin, alginate, and decellularized cardiac extracellular matrix;
   treating the PSC suspension by cross-linking to produce a three-dimensional PSC microenvironment; and
   culturing the three-dimensional PSC microenvironment to differentiate the PSCs into a cardiac tissue.

2. The method of claim 1, wherein treating the PSC suspension further comprises placing the PSC suspension into a mold prior to cross-linking.

3. The method of claim 1, wherein the three-dimensional PSC microenvironment is selected from the group consisting of microislands, cardiac discs, strings, macrotissues, and microspheres, and combinations thereof.

4. The method of claim 1, wherein treating the PSC suspension to produce a three-dimensional PSC microenvironment comprises covalently cross-linking the hydrogel precursor solution.

5. The method of claim 4, wherein covalently cross-linking the hydrogel precursor solution comprises photo-crosslinking the hydrogel precursor solution.

6. The method of claim 5, wherein the hydrogel precursor solution comprises an accelerator and at least one photoinitiator component.

7. The method of claim 6, wherein the accelerator comprises triethanolamine (TEOA) and the at least one photoinitiator component comprises Eosin Y.

8. The method of claim 1 wherein the PSCs are human induced PSCs (hiPSCs).

9. The method of claim 1, wherein the natural hydrogel-forming component is fibrinogen, and combining the population of PSCs with a hydrogel precursor solution comprises combining from 30 to 60 million PSCs per milliliter of hydrogel precursor solution.

10. The method of claim 1, wherein culturing the three-dimensional PSC microenvironment to differentiate the PSCs into cardiac tissue does not include electrically or mechanically stimulating the three-dimensional PSC microenvironment.

11. The method of claim 1, wherein the hydrogel precursor solution comprises acrylated PEG and fibrinogen.

12. The method of claim 1, wherein the acrylate component comprises acrylated gelatin.

13. The method of claim 1, wherein the acrylate component comprises a PEG-diacrylate.

14. The method of claim 1, wherein treating the PSC suspension by cross-linking to produce a three-dimensional PSC microenvironment further comprises cross-linking until the three-dimensional PSC microenvironment reaches a stiffness of less than 500 Pascals.

15. The method of claim 14, further comprising cross-linking until the three-dimensional PSC microenvironment reaches a stiffness of from 38 to 292 Pascals.

* * * * *